US008092537B2

(12) United States Patent
McGahan et al.

(10) Patent No.: US 8,092,537 B2
(45) Date of Patent: Jan. 10, 2012

(54) ANTERIOR IMPACTED BONE GRAFT AND DRIVER INSTRUMENTS

(75) Inventors: Thomas V. McGahan, Memphis, TN (US); Steven D. DeRidder, Bartlett, TN (US); Dayna Buskirk, Gainesville, FL (US); Eric C. Lange, Germantown, TN (US)

(73) Assignees: Warsaw Orthopedic, Inc., Warsaw, IN (US); RTI Biologics, Inc., Alachua, FL (US)

( * ) Notice: Subject to any disclaimer, the term of this patent is extended or adjusted under 35 U.S.C. 154(b) by 35 days.

(21) Appl. No.: 12/592,698

(22) Filed: Dec. 1, 2009

(65) Prior Publication Data

US 2010/0087875 A1 Apr. 8, 2010

Related U.S. Application Data

(60) Division of application No. 11/437,392, filed on May 19, 2006, now Pat. No. 7,635,371, and a continuation of application No. 11/030,459, filed on Jan. 5, 2005, now abandoned, which is a division of application No. 10/213,328, filed on Aug. 6, 2002, now Pat. No. 6,984,245, which is a continuation of application No. PCT/US01/05638, filed on Feb. 22, 2001.

(60) Provisional application No. 60/183,930, filed on Feb. 22, 2000.

(51) Int. Cl.
*A61F 2/44* (2006.01)
(52) U.S. Cl. .................................. 623/17.11
(58) Field of Classification Search .... 623/17.11–17.16; 606/249
See application file for complete search history.

(56) References Cited

U.S. PATENT DOCUMENTS

| 985,269 A | 2/1911 | McIntyre et al. |
| 4,165,746 A | 8/1979 | Burgin |
| 4,714,469 A | 12/1987 | Kenna |
| 4,997,432 A | 3/1991 | Keller |
| 5,088,472 A | 2/1992 | Fakhrai |
| 5,192,327 A | 3/1993 | Brantigan |
| 5,397,364 A | 3/1995 | Kozak et al. |
| 5,522,899 A | 6/1996 | Michelson |
| 5,609,635 A | 3/1997 | Michelson |
| 5,776,199 A | 7/1998 | Michelson |
| 5,782,919 A | 7/1998 | Zdeblick et al. |
| 5,797,917 A | 8/1998 | Boyd et al. |
| 5,885,299 A | 3/1999 | Winslow et al. |
| 5,888,227 A | 3/1999 | Cottle |
| 5,895,426 A | 4/1999 | Scarborough et al. |
| 6,019,793 A | 2/2000 | Perren et al. |
| 6,083,225 A | 7/2000 | Winslow et al. |
| 6,120,502 A | 9/2000 | Michelson |
| 6,139,551 A | 10/2000 | Michelson et al. |
| 6,159,211 A | 12/2000 | Boriani et al. |
| 6,174,311 B1 | 1/2001 | Branch et al. |

(Continued)

FOREIGN PATENT DOCUMENTS

WO WO 90/00037 1/1990

(Continued)

*Primary Examiner* — Eduardo C Robert
*Assistant Examiner* — Mary Hoffman

(57) ABSTRACT

Instrument and implants are disclosed which provide for insertion of an implant into an intervertebral disc space from multiple approaches to the spine. Specifically, as a preferred aspect of the invention the implant includes a tapered portion and the implant may be inserted from multiple approaches to the spine with the orientation and taper properly oriented in the disc space regardless of the approach.

19 Claims, 22 Drawing Sheets

U.S. PATENT DOCUMENTS

| | | |
|---|---|---|
| 6,319,257 B1 | 11/2001 | Carignan et al. |
| 6,375,683 B1 | 4/2002 | Crozet et al. |
| 6,458,158 B1 | 10/2002 | Anderson et al. |
| 6,482,233 B1 | 11/2002 | Aebi et al. |
| 6,530,955 B2 | 3/2003 | Boyle et al. |
| 6,558,423 B1 | 5/2003 | Michelson |
| 6,780,192 B2 | 8/2004 | McKay et al. |
| 6,984,245 B2 | 1/2006 | McGahan et al. |
| 2001/0020170 A1 | 9/2001 | Zucherman et al. |
| 2002/0032448 A1 | 3/2002 | Houfburg |
| 2002/0133166 A1 | 9/2002 | McKay et al. |
| 2002/0165612 A1 | 11/2002 | Gerber et al. |
| 2002/0198532 A1 | 12/2002 | Michelson |
| 2003/0069586 A1 | 4/2003 | Errico et al. |
| 2003/0139815 A1 | 7/2003 | Grooms et al. |
| 2003/0216744 A1 | 11/2003 | Longhini et al. |
| 2006/0212120 A1 | 9/2006 | McGahan et al. |

FOREIGN PATENT DOCUMENTS

| | | |
|---|---|---|
| WO | WO 98/42269 | 10/1998 |
| WO | WO 99/09914 | 3/1999 |

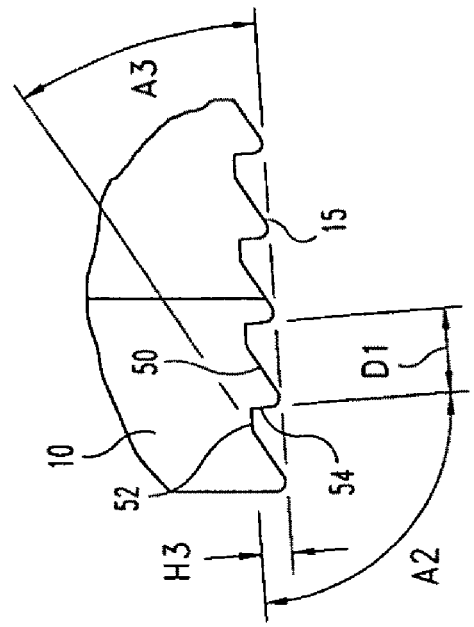
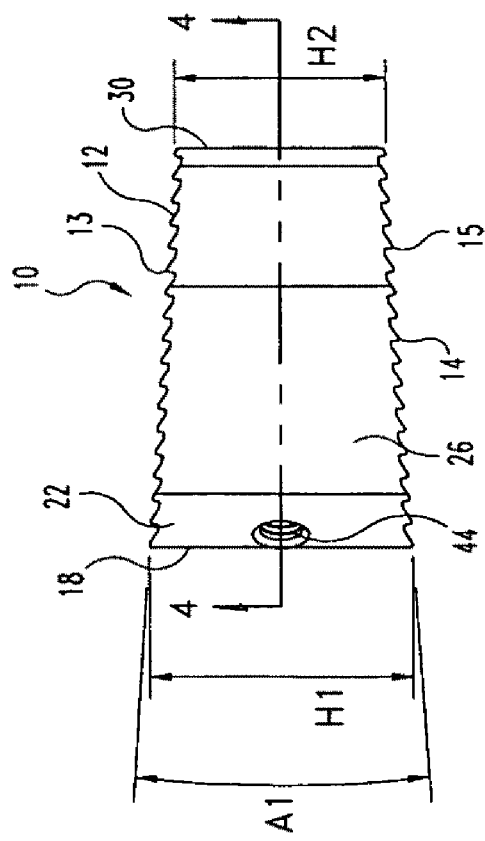
Fig. 2b
Fig. 2a

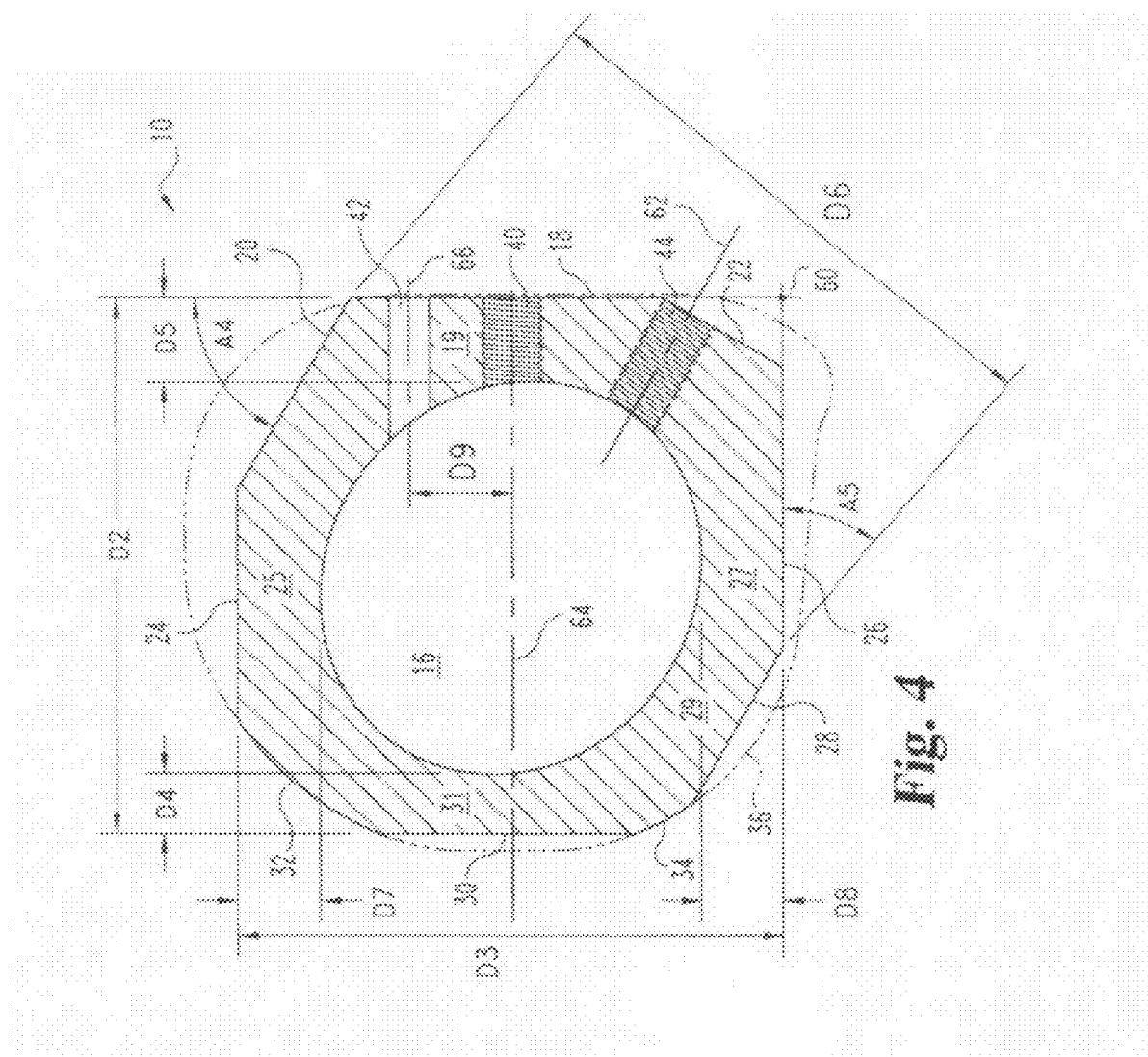
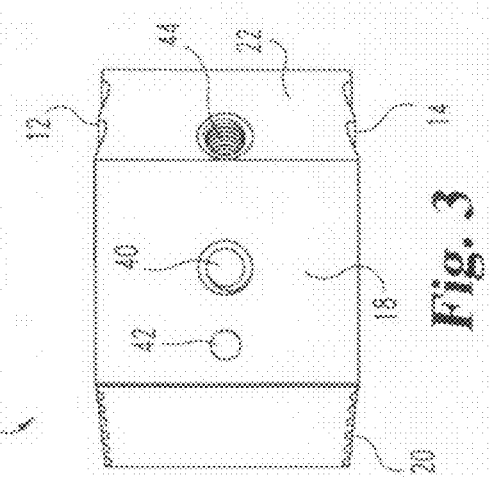
Fig. 4
Fig. 3

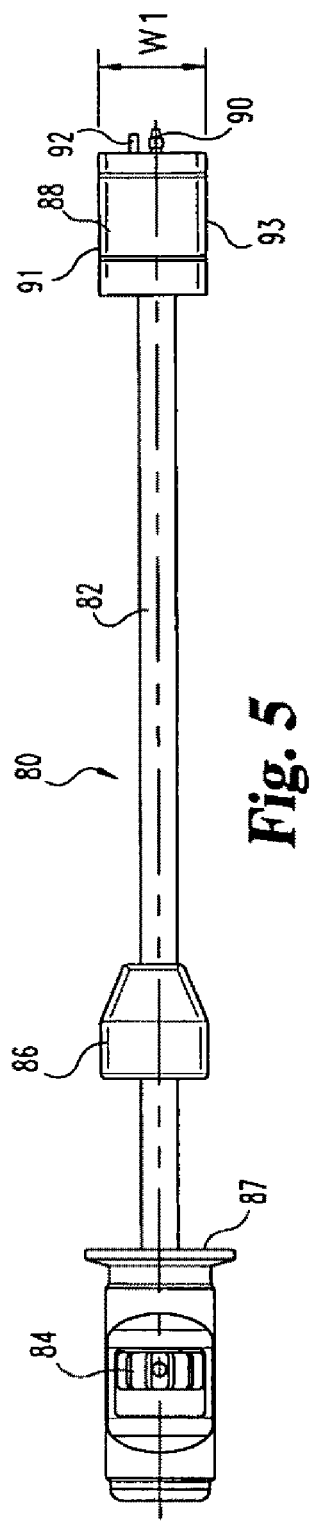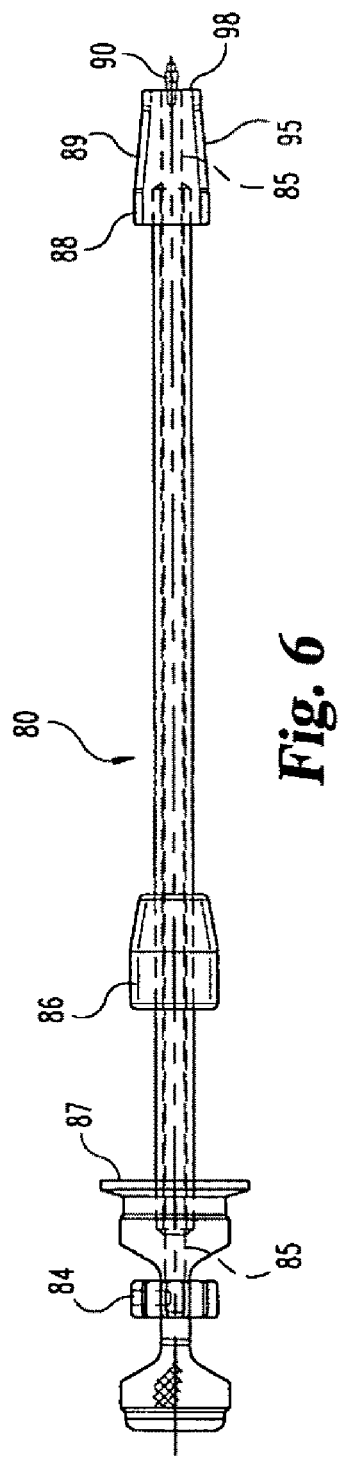

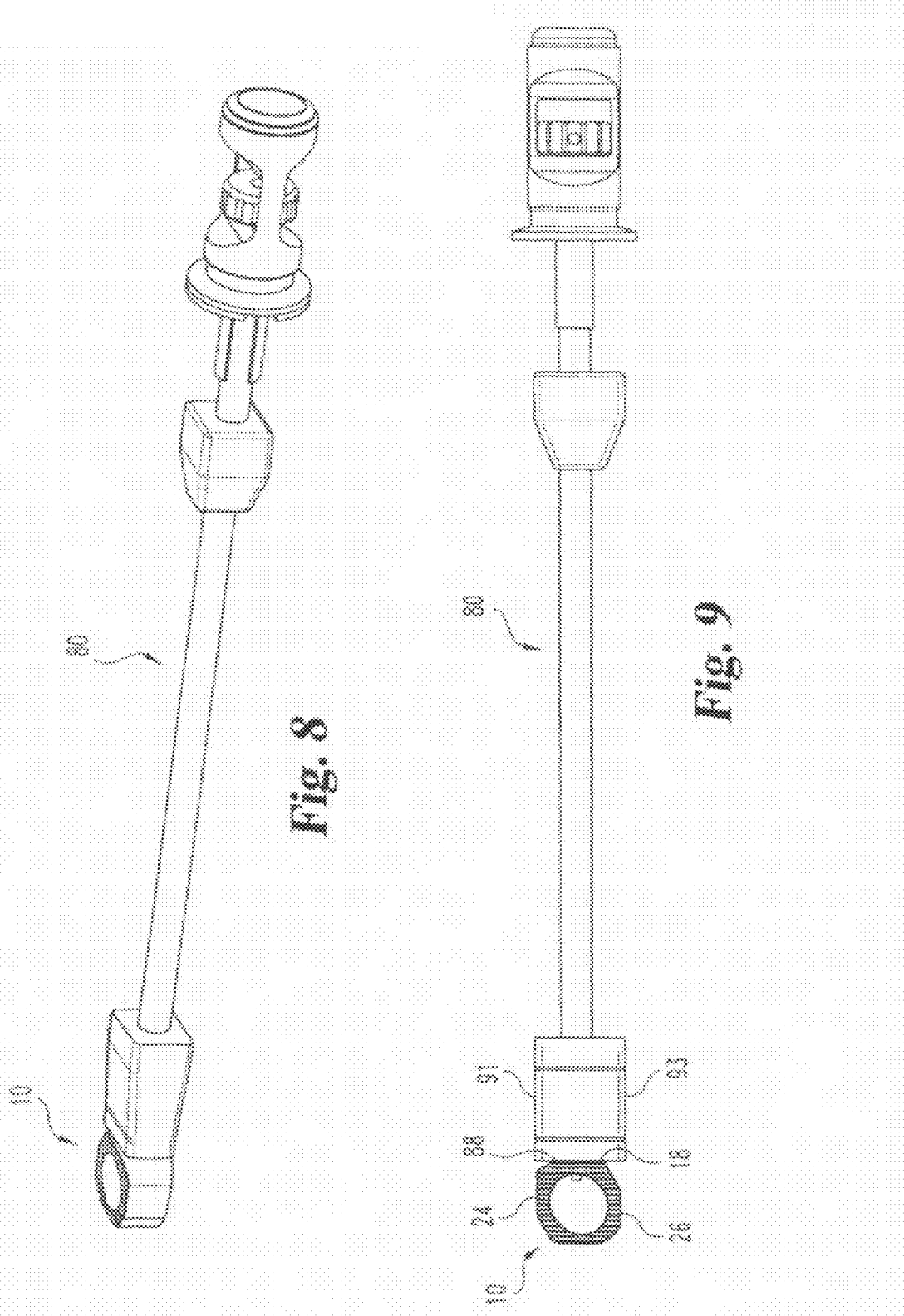

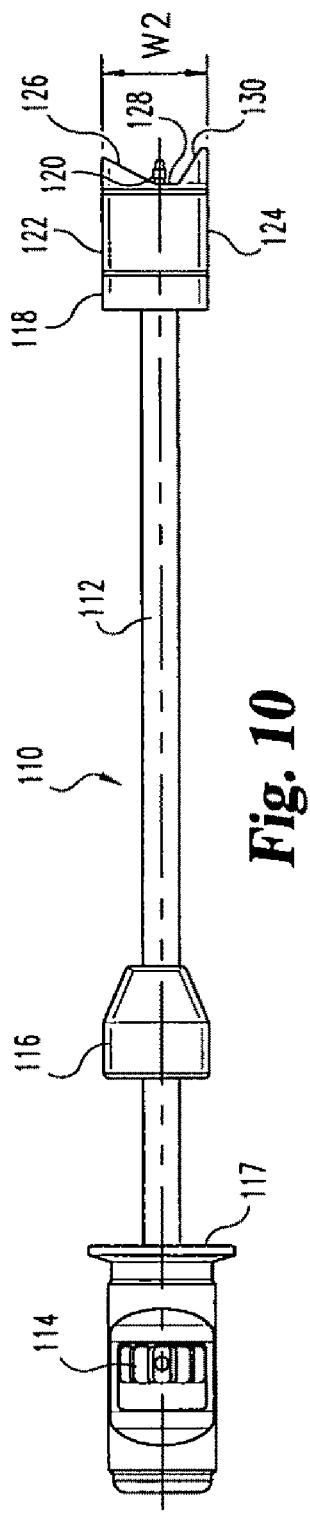
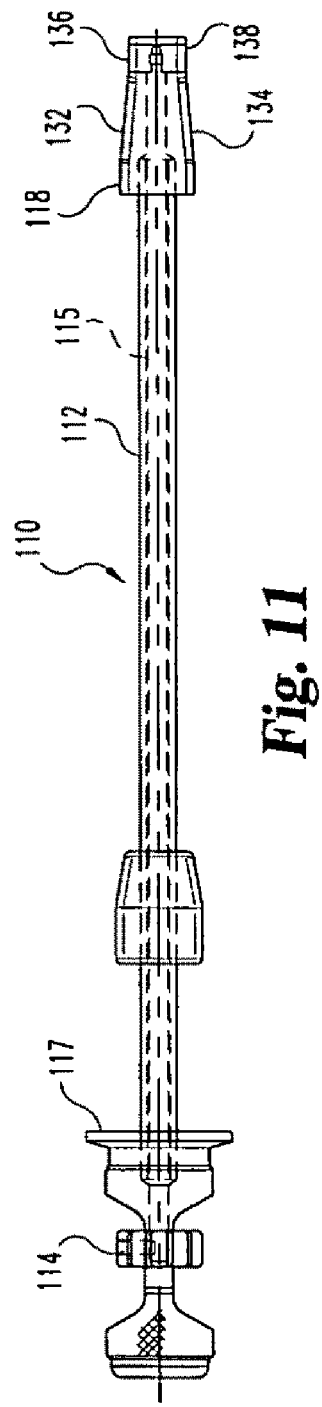

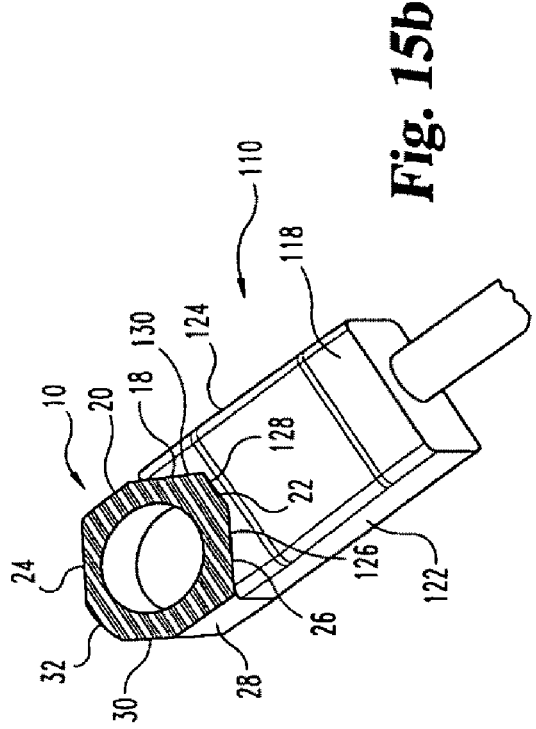
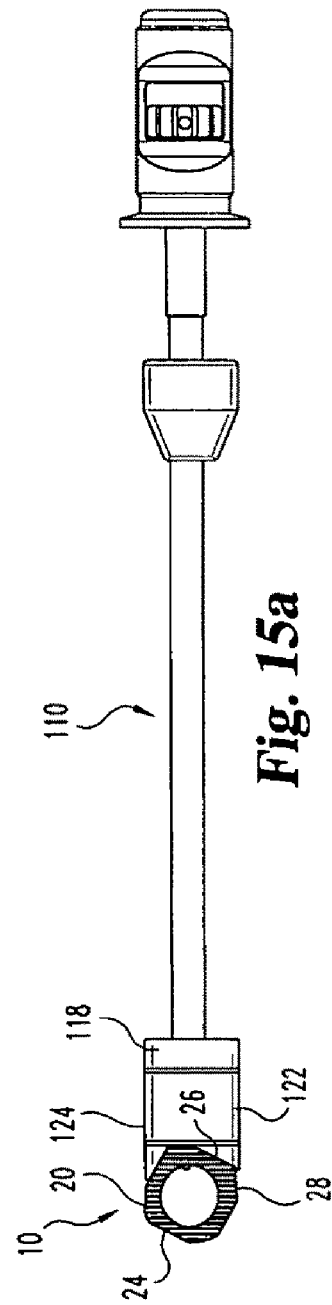
Fig. 15b
Fig. 15a

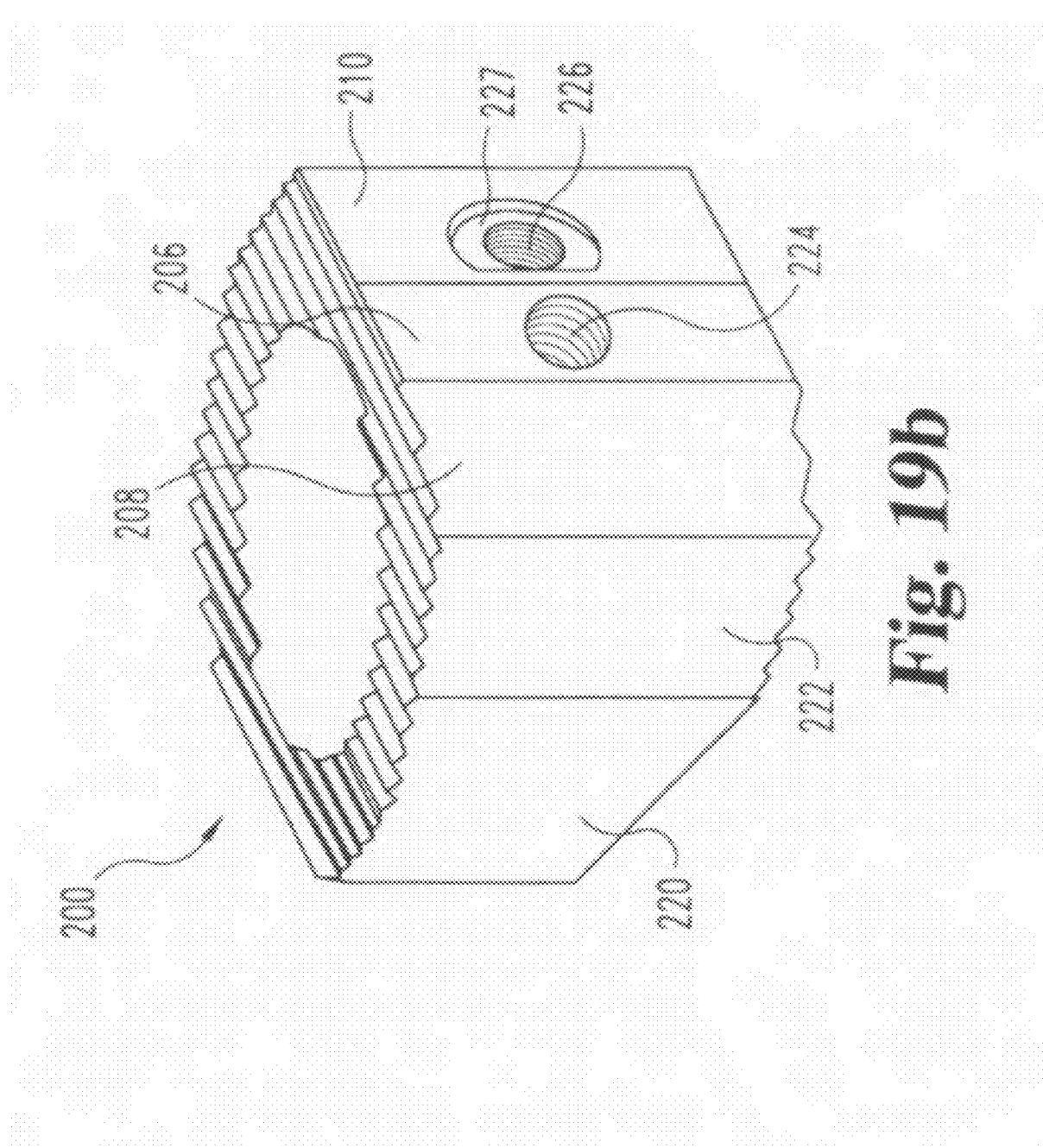

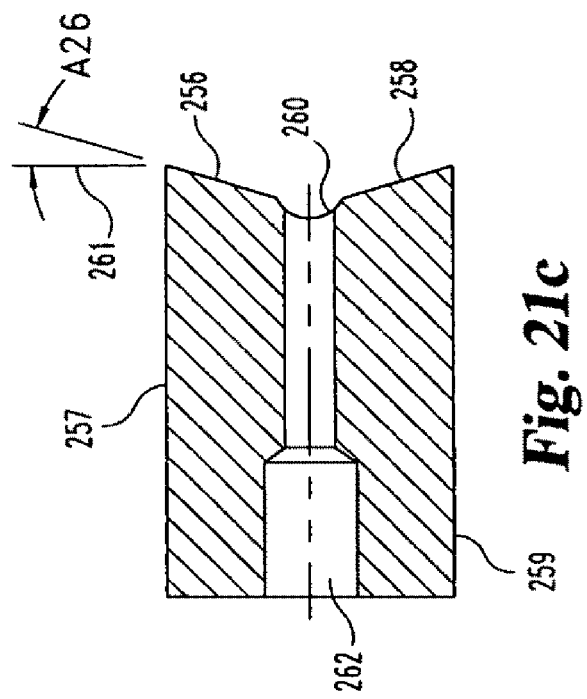
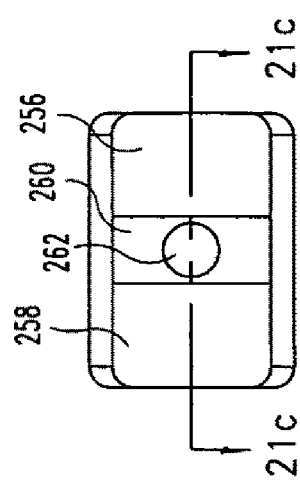
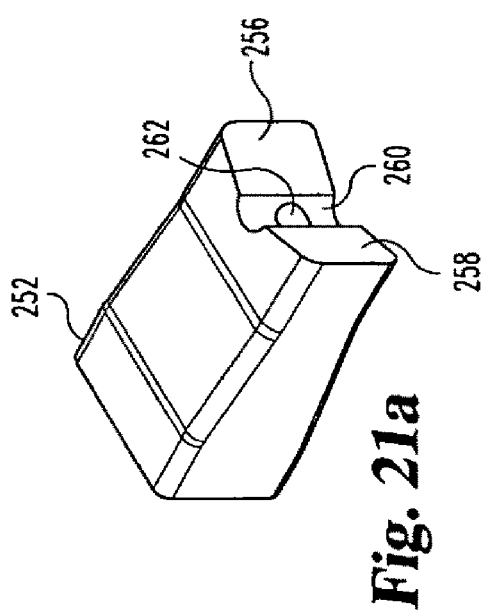
*Fig. 21c*
*Fig. 21b*
*Fig. 21a*

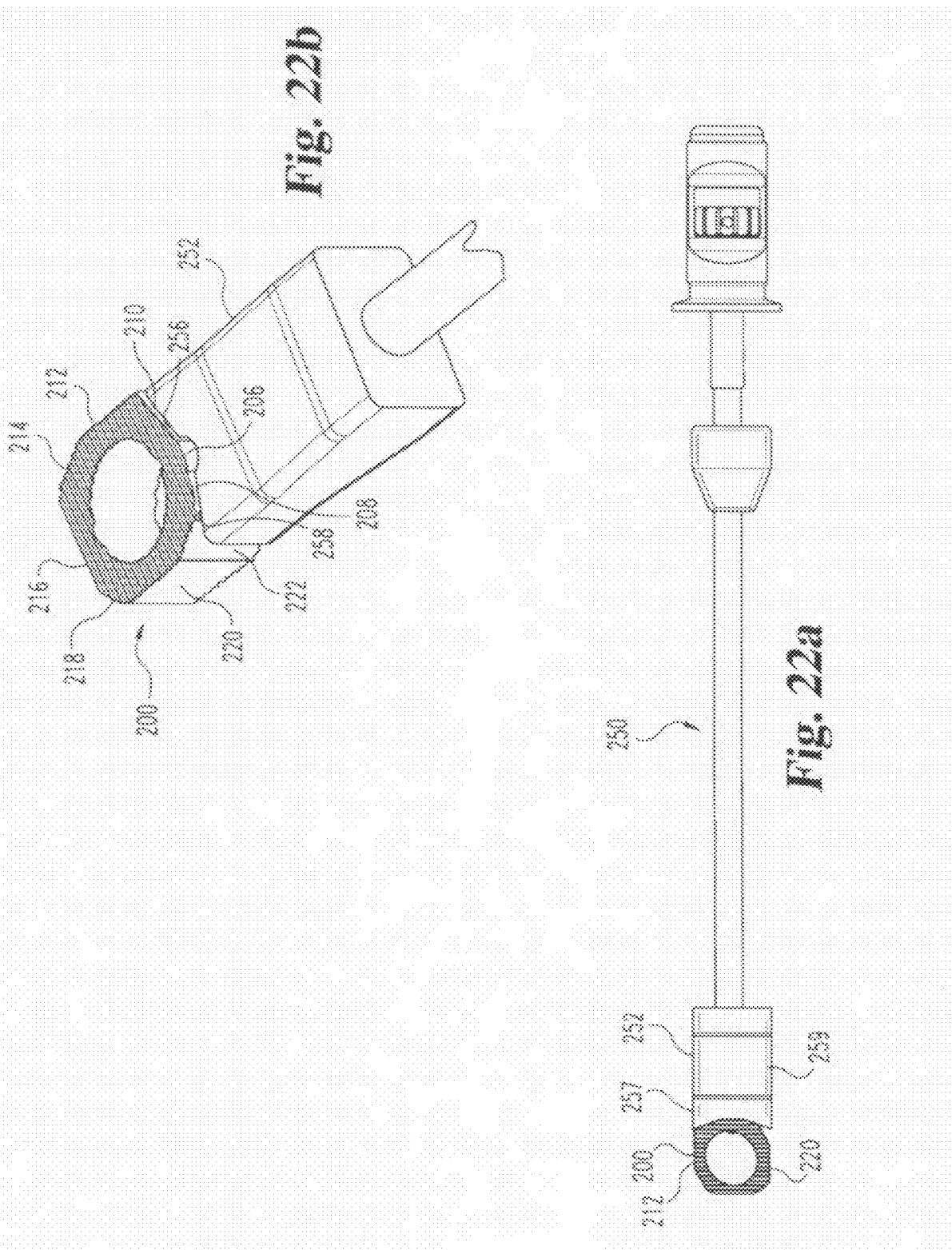

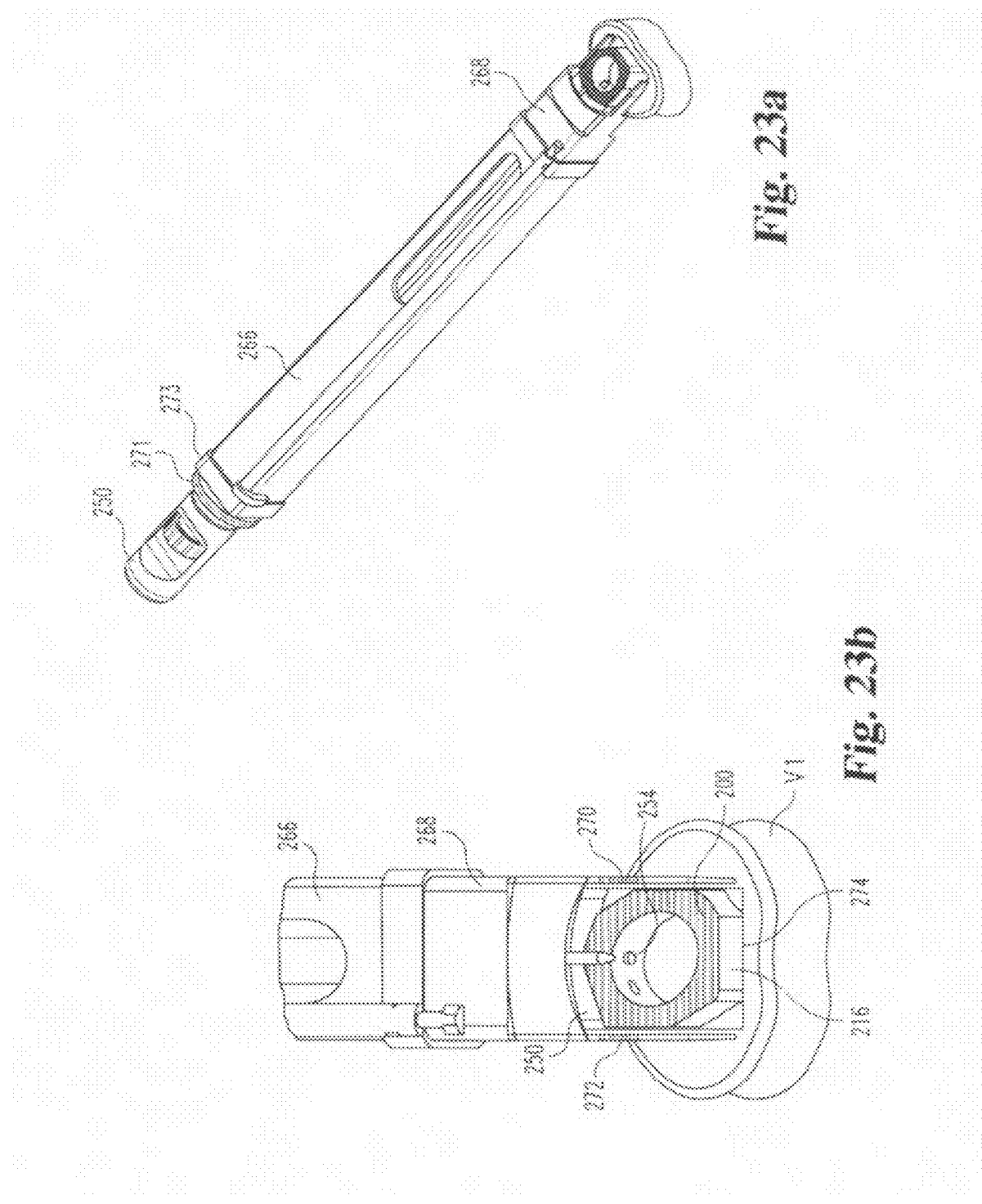

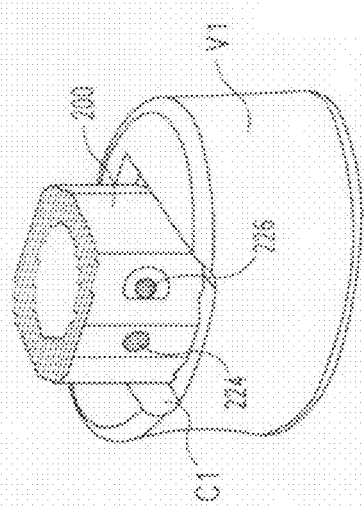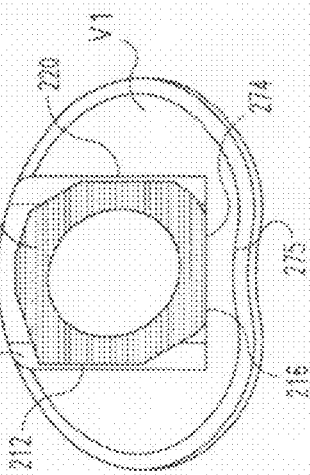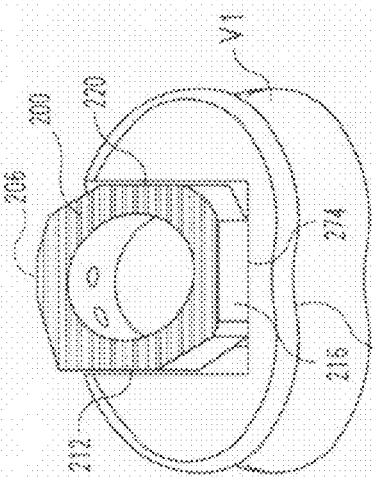

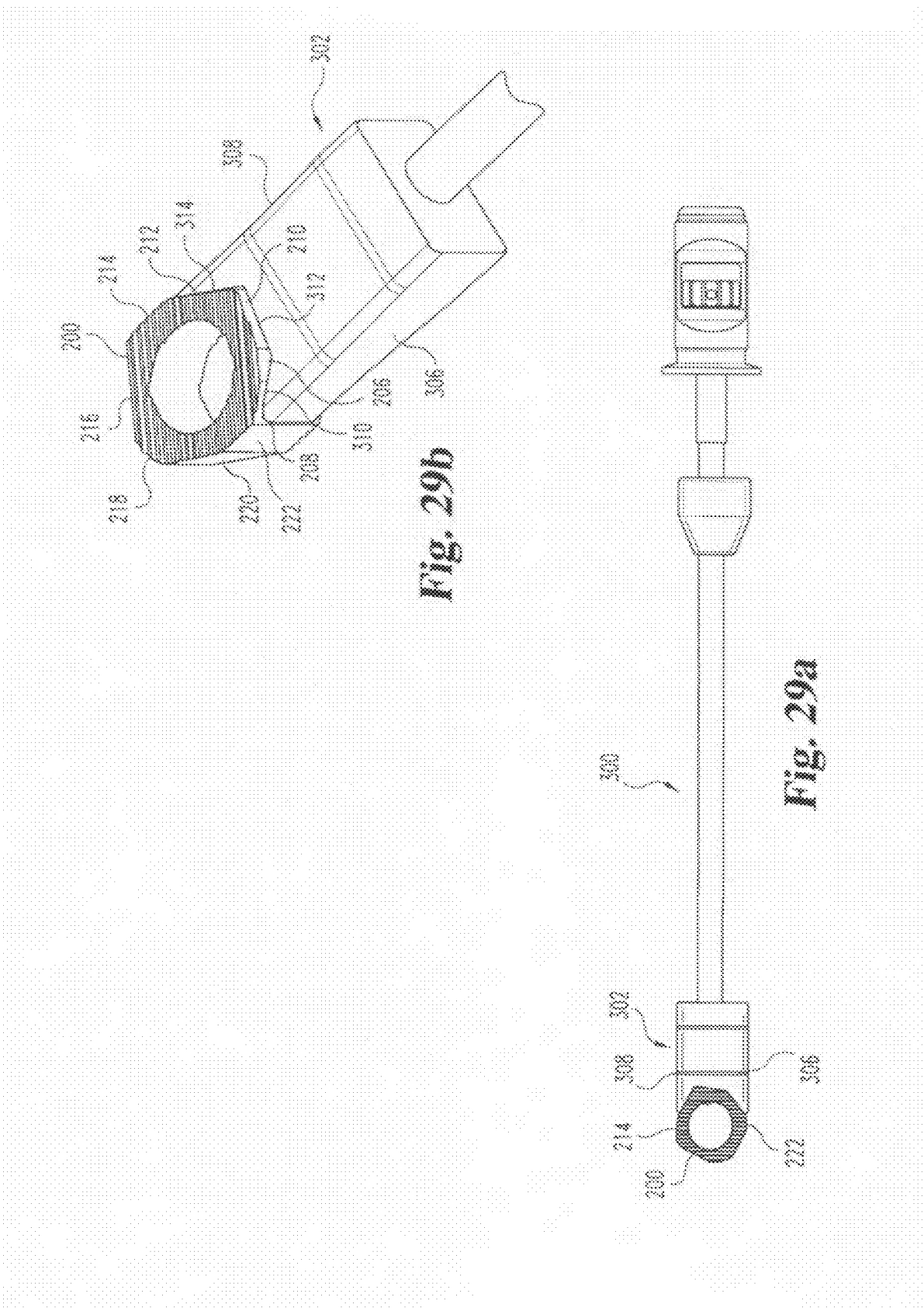

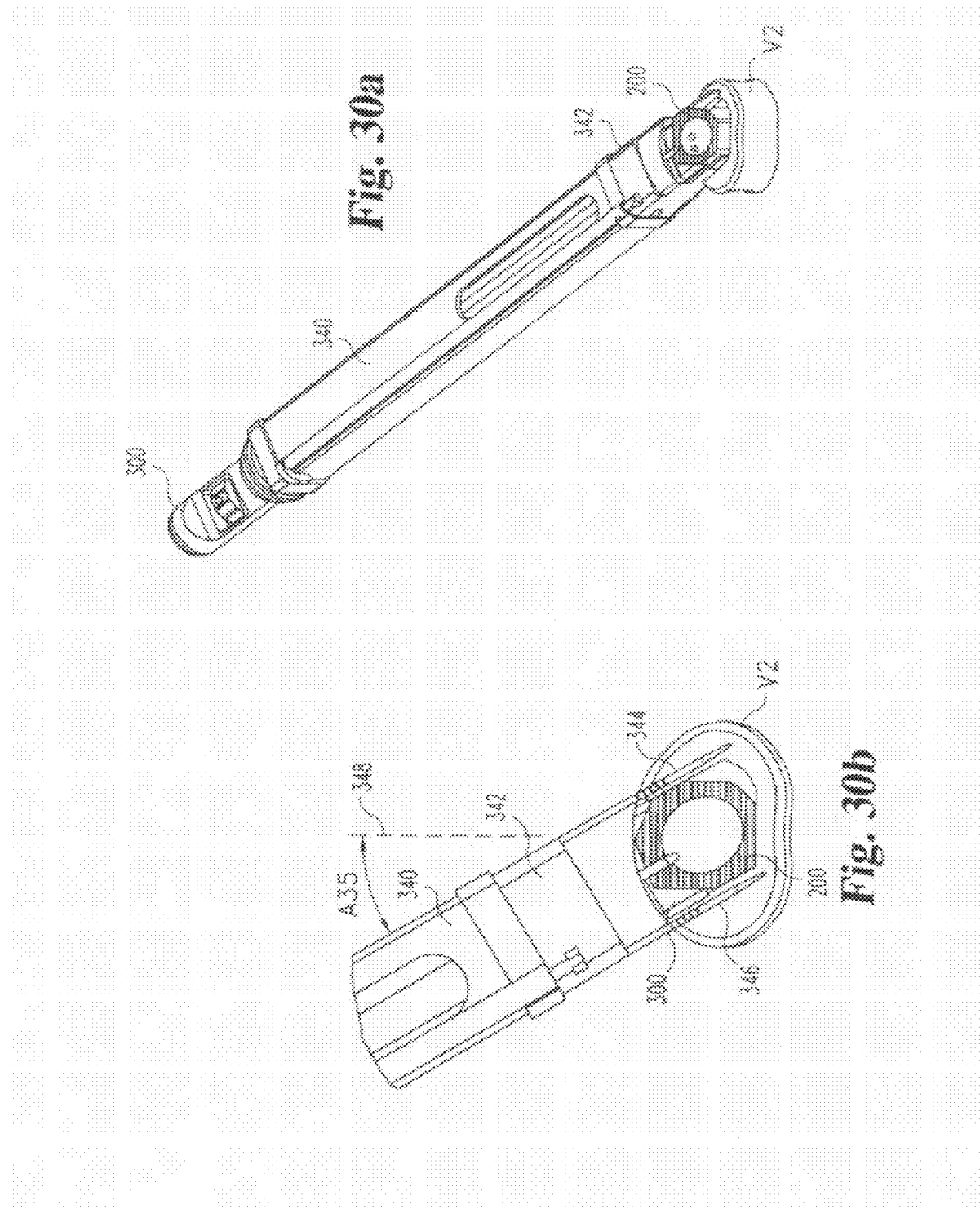

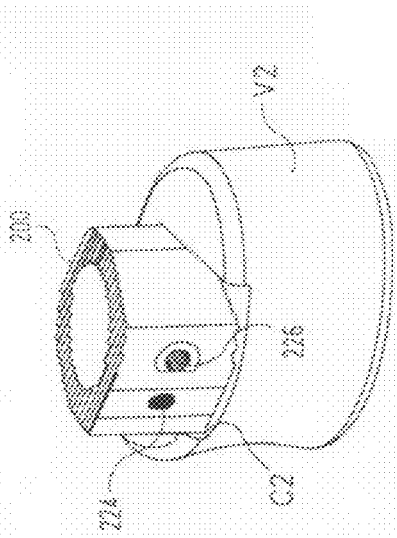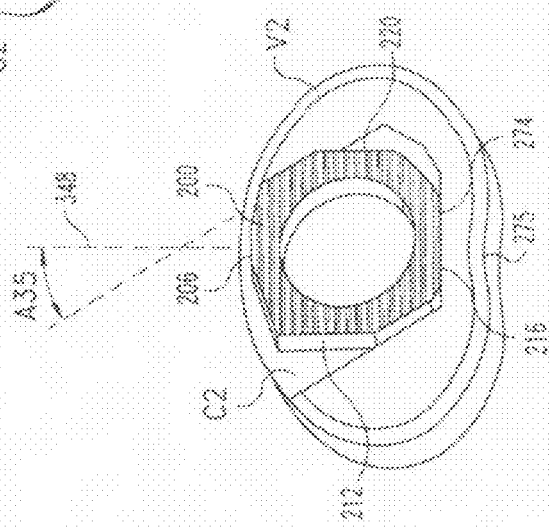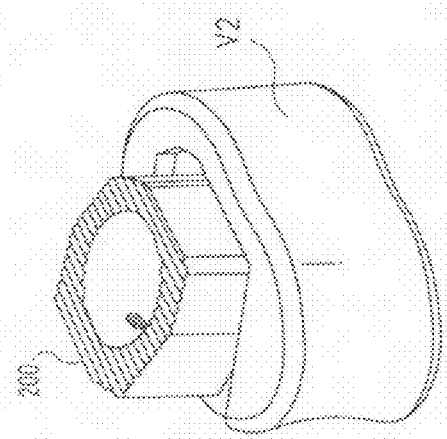

ANTERIOR IMPACTED BONE GRAFT AND DRIVER INSTRUMENTS

REFERENCE TO RELATED APPLICATIONS

The present application is a divisional of U.S. patent application Ser. No. 11/437,392 filed May 19, 2006 now U.S. Pat. No. 7,635,371, a continuation of abandoned U.S. patent application Ser. No. 11/030,459 filed Jan. 5, 2005 entitled "Anterior Impacted Bone Graft and Driver Instruments", which is a divisional of U.S. patent application Ser. No. 10/213,328 filed Aug. 6, 2002 entitled "Anterior Impacted Bone Graft and Driver Instruments" and issued as U.S. Pat. No. 6,984,245, which is a continuation of PCT Patent Application Serial No. PCT/US01/05638 filed Feb. 22, 2001 entitled "Anterior Impacted Bone Graft and Driver Instruments" which was published in English under Article 21(2) and which claims the benefit of U.S. Provisional Patent Application Ser. No. 60/183,930 filed Feb. 22, 2000 entitled "Instruments and Implants for Multi-Directional Insertion of a Vertebral Spacer". Each of the referenced applications is hereby incorporated by reference in its entirety.

BACKGROUND OF THE INVENTION

The present invention relates generally to instruments and implants for intervertebral spacing. More specifically, the present invention provides instruments and implants that may be utilized to provide multi-directional insertion techniques to establish and maintain intervertebral spacing. Still more preferably, the present invention provides implants made of bone adapted to be inserted from more than one direction while maintaining proper orientation in the disc space.

The removal of damaged or diseased discs and restoration of disc space height to treat chronic back pain and other ailments, is well-known. Spacers are often utilized to maintain or reestablish disc space height after removal of all or a portion of the disc. Such spacing implants may include those promoting fusion between adjacent vertebral bodies, inert implants, and artificial disc implants. Such implants are typically designed to be inserted from an anterior, posterior or lateral approach. However, such implants are often designed for insertion only from one of the particular approaches to the spine. This is particularly true where implants are intended to maintain non-parallel angulation between adjacent vertebrae. Therefore, multiple implants each designed for insertion from one of the various approaches to the spine must be maintained in inventory to accommodate the various surgical demands of each procedure. Maintaining multiple implant designs may create inventory problems for both manufacturers and their customers. Moreover, the complications of creating multiple implants to accomplish the same desired spacing is compounded when implants are made of a scarce resources, such as allograft bone.

Therefore, there remains a need for instruments, techniques, and implants that reduce implant inventory without sacrificing desired implant configurations.

SUMMARY OF THE INVENTION

The present invention provides for instruments to implant a single implant design from multiple approaches to the disc space. In a preferred aspect of the present invention, instruments are provided for inserting an implant from a direct anterior approach to the spine and from an oblique-anterior approach to the spine.

In a further aspect of the present invention, an implant is provided that includes features permitting insertion into the disc space from multiple directions. In a preferred aspect of the present invention, the implant may be configured for insertion from a direct anterior approach as well as an anterior-lateral approach to the spine. Still more preferably, the anterior-lateral approach to the spine is from an oblique angle with respect to the sagittal plane.

In still a further aspect of the present invention, a multi-faceted implant is provided comprising an implant body having a first pair of substantially parallel side walls and a second pair of substantially parallel side walls. The second pair of substantially parallel side walls are disposed at an oblique angle with respect to the first pair of substantially parallel side walls. The angulation between the first and second set of parallel side walls permits insertion of the implant into the disc space from multiple directions. Further in one preferred embodiment the distance between the first pair of side walls is substantially identical to the distance between the second pair of side walls. One choice is to dispose the second pair of side walls at an angle of approximately 30 degrees with respect to the first pair of side walls. In a more preferred aspect of the present invention, the implant body has upper and lower bone engaging surfaces that are tapered to maintain angulation between adjacent vertebrae. In still further preferred aspects of the invention, one of each of the first and second pair of side walls includes an insertion tool bore.

In yet a further aspect of the present invention, a method of making an implant of boney material is provided. The method comprises forming a first pair of substantially parallel side walls on the boney material. A second pair of substantially parallel side walls is formed at an oblique angle with respect to the first pair of side walls. In one aspect the method further includes forming a plurality of driving surfaces on the donor bone. Still more preferably, the upper and lower bone engaging surfaces are disposed at an angle with respect to each other.

In still a further aspect of the invention an implant inserter is provided. Preferably, the implant inserter includes anti-rotation components to limit rotation of the implant about the longitudinal axis of the inserter and rotation about the axis of the implant itself. In one preferred embodiment, the anti-rotation components comprise a pair of angled side walls on the inserter adapted to engage a pair of corresponding surfaces on the implant. In still a further preferred aspect, a threaded post engages a corresponding opening on the implant and the angled surfaces are spaced from the opening to limit stress placed on the implant adjacent the opening.

These and other objects of the present invention will become apparent from the following description of the preferred embodiments.

BRIEF DESCRIPTION OF THE DRAWINGS

FIG. 2(a) is a side view of the implant of FIG. 1.

FIG. 2(b) is an enlarged view of a portion of FIG. 2(a).

FIG. 3 is an end view of the implant of FIG. 1.

FIG. 4 is a cross-sectional view taken along line 4-4 of FIG. 2(a).

FIG. 5 is a top view of an implant inserter according to the present invention.

FIG. 6 is a side view of the implant inserter of FIG. 5.

FIG. 8 is a perspective view of an implant and an implant inserter according to the present invention.

FIG. 9 is a top view of the combination shown in FIG. 8.

FIG. 10 is a top view of a further embodiment of an implant inserter according to the present invention.

FIG. 11 is a side view of the implant inserter of FIG. 10.

FIG. 15(a) is a top view of an implant and an implant inserter according to the present invention.

FIG. 15(b) is an enlarged perspective view of a portion of FIG. 15(a).

FIG. 19(b) is a perspective view of the implant of FIG. 16.

FIG. 21(a) is a perspective view of the distal guide of the implant inserter of FIG. 20(a).

FIG. 21(b) is an end view of the distal guide of FIG. 21(a).

FIG. 21(c) is a cross-sectional view of the distal guide of FIG. 21(b) taken along line 21(c)-21(c).

FIG. 22(a) is a top view of an implant inserter and an implant according to the present invention.

FIG. 22(b) is an enlarged perspective view of a portion of the drawing FIG. 22(a).

FIG. 23(a) is a perspective view of an implant inserter, implant, and guide tube according to the present invention.

FIG. 23(b) is an enlarged perspective view of a portion of FIG. 23(a).

FIG. 24(a) is a perspective view of an implant positioned adjacent a vertebral body according to the present invention.

FIG. 24(b) is a top view of the implant and vertebral body of FIG. 24(a).

FIG. 24(c) is a further perspective view of the implant and vertebral body of FIG. 24(a).

FIG. 29(a) is a top view of an implant and an implant inserter according to the present invention.

FIG. 29(b) is an enlarged perspective view of a portion of FIG. 29(a).

FIG. 30(a) is a perspective view of an implant, implant inserter, and guide tube according to one aspect of the present invention.

FIG. 30(b) is an enlarged top view of a portion of FIG. 30(a).

FIG. 31(a) is a perspective view of an implant positioned adjacent a vertebral body according to the present invention.

FIG. 31(b) is a top perspective view of the implant and vertebral body of FIG. 31(a).

FIG. 31(c) is a further perspective view of the implant and vertebral body of FIG. 31(a).

DESCRIPTION OF THE PREFERRED EMBODIMENTS

Figure 1:
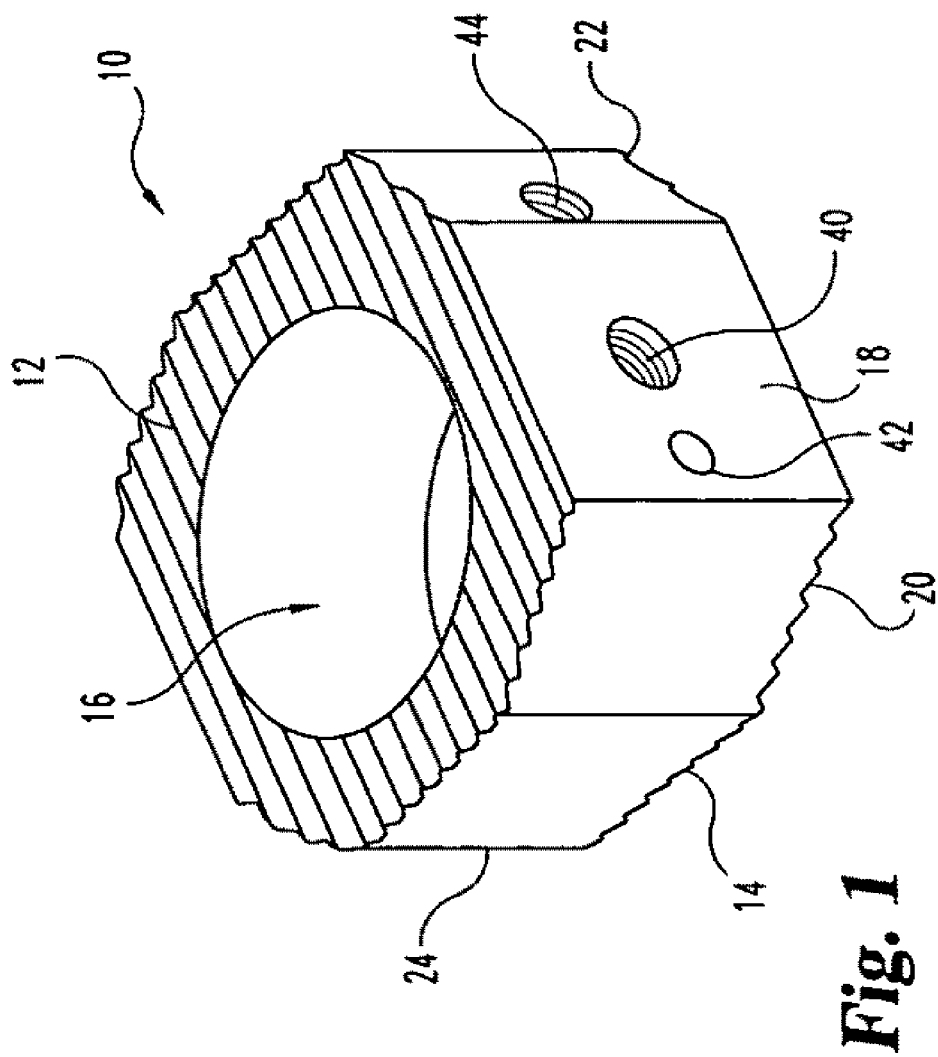
FIG. 1 is a perspective view of an implant according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The present invention provides implants and instruments for multi-directional implantation of an intervertebral spacer. Additional instrumentation and techniques for disc space preparation are disclosed in Provisional Application entitled "Instruments and techniques for Disc Space Preparation," filed Feb. 22, 2000. The disclosure of the referenced Provisional Application is incorporated herein by reference in its entirety. Referring now to FIGS. 1-4, there is shown an implant according to a preferred embodiment of the present invention. Implant 10 includes an upper bone engaging surface 12, a lower bone engaging surface 14, and a central opening 16 extending from upper surface 12 to lower surface 14. While it is contemplated that implant 10 may be formed of any suitable bio-compatible material (e.g. steel, titanium, composites, ceramics, zenograft, composite bone material, etc.), in a preferred aspect of the invention, implant 10 is formed of allograft bone. Referring specifically to FIG. 4, outline 36 represents a typical outline of an allograft ring suitable for use to form an implant according to the present invention. It will be understood that central opening 16 conforms generally to the medullary canal, typically found in an allograft ring.

Implant 10 includes a pair of opposing side walls 24 and 26 formed in substantial parallel alignment with longitudinal axis 64. A further pair of oblique angled side walls 20 and opposing side wall 28 are formed at an angle A5 with respect to side walls 26 and 24. In a preferred embodiment, angle A5 is approximately 30 degrees. In a preferred aspect, from driving wall 18 extends substantially perpendicular to longitudinal axis 64 and at an angle of A4 with respect to angled surface 20. In a preferred embodiment, angle A4 is substantially 60 degrees. Implant 10 includes a front face 18 and an opposing end face 30. While not required, front face 18 and face 30 are planar surfaces in substantially parallel alignment. Further, front face 18 is substantially parallel to end face 30. A first opening 40 is formed in implant 10 and is internally threaded to receive an externally threaded post. Internally threaded opening 40 extends substantially along longitudinal axis 64 and in substantial alignment with side walls 24 and 26. A second bore 42 has an axis 66 extending substantially parallel to axis 64 and spaced at a distance D9 therefrom. Bore 42 is adapted to receive a substantially smooth pin. It will be understood that a pin extending in bore 42 will limit the tendency of implant 10 to rotate as an externally threaded rod is inserted into threaded opening 40. In a preferred aspect, distance D9 is approximately 5 mm.

Referring now to FIG. 4, front face 18 and opposing end face 30 are substantially parallel and spaced by distance D2. In a preferred aspect, opposing side walls 24 and 26 are substantially parallel and spaced by a distance of D3. Opposing angled walls 20 and 28 are substantially parallel and spaced by a distance D6. In a preferred embodiment, distances D2, D3, and D6 are approximately equal. Still more preferably, in at least one preferred embodiment adapted for implantation in the lumbar spine, distances D2, D3, and D6 are approximately 26 mm.

Referring still further to FIG. 4, an angled driving wall 22 is provided at an approximately 30 degree angle with respect to front wall 18. Internally threaded bore 44 extends through angled wall 22 along axis 62. Axis 62 is substantially parallel to side walls 20 and 28.

As shown most clearly in FIG. 4, the multi-faceted implant provides three pairs of substantially parallel side walls. A reference point 60 is provided on the drawing as an indication of the starting point of the formation of the various walls of the implant. Side wall portions 32 and 34 are not machined, thereby preserving at least a portion of the original configuration of the donor bone. It will be understood that the amount of machining required to form an implant according to the present invention depends in large measure on the configuration of the donor bone available and the dimensions of the implant intended to be manufactured from the available donor bone. As will be explained further herein, it is advantageous in a preferred embodiment that the maximum outer dimensions of the implant permit the implant to be inserted from a direct anterior approach to the spine, an oblique angle to the spine and, while not specifically shown in the drawings, a lateral approach to the spine.

Dimensions of donor bone vary depending on the source of the bone, as well as the specific location of the source of an allograft ring taken along a bone, such as the femur. In one aspect of the invention, intended for use in the lumbar spine, it is preferred that the implant have certain minimal dimensions for the safety and efficacy of the device. While such dimensions are disclosed herein, it is contemplated that dimensions may be altered for various implants in the lumbar, thorasic, and cervical spine without deviating from the present invention provided that the implant provides the desired strength and stability. Specifically, minimum dimensions are given from the surface of the outer side walls to central channel 16. As previously indicated, central channel 16 is preferably defined by the naturally occurring medullary canal. However, it may be altered or increased by additional machining to form a channel having desired dimensions or shapes. Side wall 19 has a dimension D5. Side wall 25 has a dimension D7. Side wall 31 has a dimension D4. Side wall 27 has a dimension D8. In a preferred aspect, dimensions D5, D7, and D8 are limited to a minimum thickness of 4 mm. Dimension D4 may have an even smaller minimum thickness of approximately 3 mm.

Referring now to FIG. 2(a), implant 10 includes end wall 30 having a height H2 and front wall 18 having a height H1. In a preferred aspect, height H1 is substantially greater than height H2. Furthermore, opposing bone engaging surfaces 12 and 14 substantially, uniformly taper from height H1 at end wall 30 to height H2 at front wall 18. In a preferred embodiment, height H1 is approximately 17 mm. Further, the substantially uniform taper between the upper and lower surfaces 12 and 14 creates an angle A1. In a particular application, angle A1 is approximately 8 degrees.

In a preferred embodiment, upper surface 12 includes buttressed ridges 13 providing an anti-migration surface to engage adjacent vertebral bone upon insertion and limit movement out of the disc space. In a similar fashion, lower bone engaging surface 14 includes a plurality of buttressed bone engaging ridges 15. Bone engaging ridges 15 are shown in greater detail in FIG. 2(b). The bone engaging ridges include a leading angled surface 50 and a trailing surface 54 disposed substantially perpendicular to the intervening flat surface 52 disposed between ridges. Angled surface 50 is disposed at an angle A3, which in a preferred embodiment is substantially 30 degrees. Trailing surface 54 is disposed at an angle A2, which in a preferred embodiment is substantially 90 degrees. Individual ridges have a height of approximately H3, which in a preferred embodiment is approximately 0.5 mm. Further, individual ridges are spaced by a distance of approximately 1.5 mm, as shown by dimension D1.

The present invention further includes an implant inserter, such as that shown in FIGS. 5 and 6. Implant inserter 80 includes an outer shaft 82 and an inner shaft 85 rotatably disposed therein. Inner shaft 85 includes a thumb wheel 84 connected to its proximal end and an externally threaded portion 90 on the distal end. Implant inserter 80 further includes a proximal guide 86, a distal guide 88, and a stop 87. The proximal and distal guides are intended to guide and maintain alignment of the inserter within an outer guide sleeve (not shown) while stop 87 provides the function of limiting further movement of the implant inserter into the outer guide sleeve (see FIG. 23a), thereby limiting the advancement of the implant into the disc space. While the implant inserter is shown with features suitable for use with a guide sleeve, it is contemplated that the inserter may be used without a guide sleeve.

Figure 7:
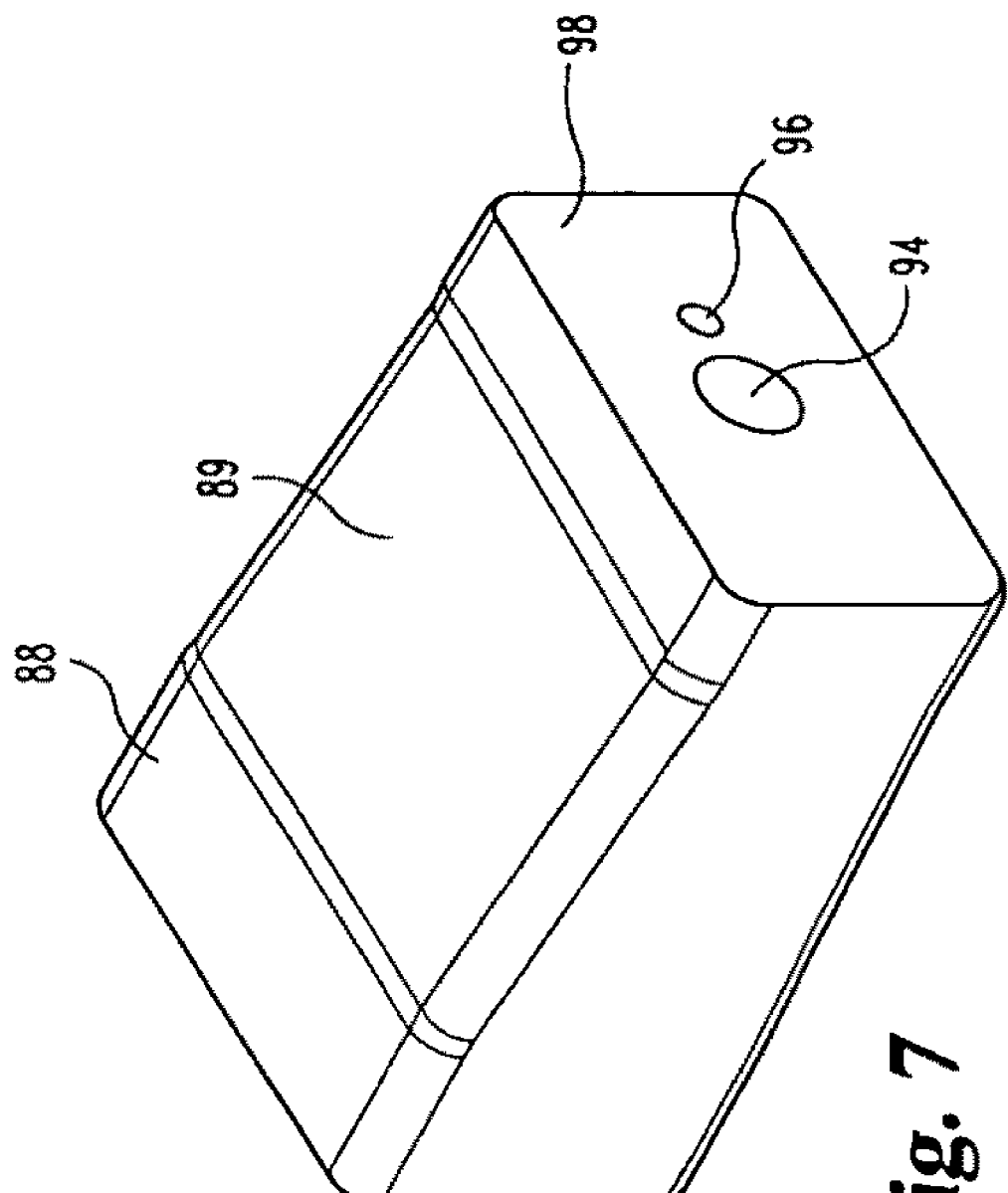
FIG. 7 is a perspective view of a distal guide of the implant inserter of FIG. 5.

Distal guide 88 includes upper and lower tapered guiding surfaces 89 and 95, respectively. Guide 88 also includes substantially parallel opposed side walls 91 and 93. Guide 88 has a width W1 extending between side walls 91 and 93. Further, with reference to FIG. 7, a substantially smooth pin 92 extends from opening 96 while inner shaft 85 extends through opening 94 of guide 88. Guide 88 includes a substantially planar bearing wall 98 extending substantially perpendicular to the longitudinal axis of the implant inserter.

Referring now to FIGS. 8 and 9, the implant inserter of FIGS. 5 and 6 is shown interconnected with the implant of FIGS. 1-4. Implant inserter 80 is interconnected with implant 10 by threaded engagement of externally threaded portion 90 of inner shaft 85 with the internally threaded opening 40 of implant 10. Further, pin 92 may be inserted into bore 42 to limit rotation of implant 10 while externally threaded portion 90 is threadedly inserted into internally threaded bore 40. Pin 92 also limits rotation of the implant about its own axis as force is applied to advance the implant into the disc space. Front face 18 is in substantial abutting engagement with bearing wall 98 such that implant 10 may be impacted into a disc space by forcing bearing wall 98 against front face 18. Furthermore, substantially parallel side walls 24 and 26 of the implant are in substantial alignment with side walls 91 and 93 of the implant inserter. In a preferred aspect, the width W1 of distal guide 88 is substantially equal to or greater than the width D3 of implant 10. The implant inserter FIGS. 8 and 9 may be referred to as a straight inserter as it is intended to function in a preferred aspect of the invention from a direct or straight anterior approach to the spine.

In still another aspect of the invention, an oblique inserter is shown in FIGS. 10 and 11. The oblique inserter is configured for engaging the implant of FIGS. 1-4 to permit insertion from an oblique angle to the spine. As a general reference, this approach may be carried out by approaching the disc space in substantial alignment with the axial plane and at an oblique angle with respect to the sagittal plane. Oblique inserter 110 includes an outer shaft 112 and an inner shaft 115 movably disposed therein. Inner shaft 115 includes a proximal thumb wheel 114 and has a distal end 120 with an external thread pattern. Inserter 110 includes proximal guide 116, distal guide 118, and stop 117. Distal guide 118 includes opposing tapered surfaces 132 and 134 tapering from opposing upper and lower surfaces 136 and 138, respectively. Distal guide 118 has a maximum width W2 extending from opposing side surfaces 122 and 124. The features of implant 110 are substantially similar to the features of implant inserter 180 with the exception of the driving surfaces of distal guide 118.

Figure 14:
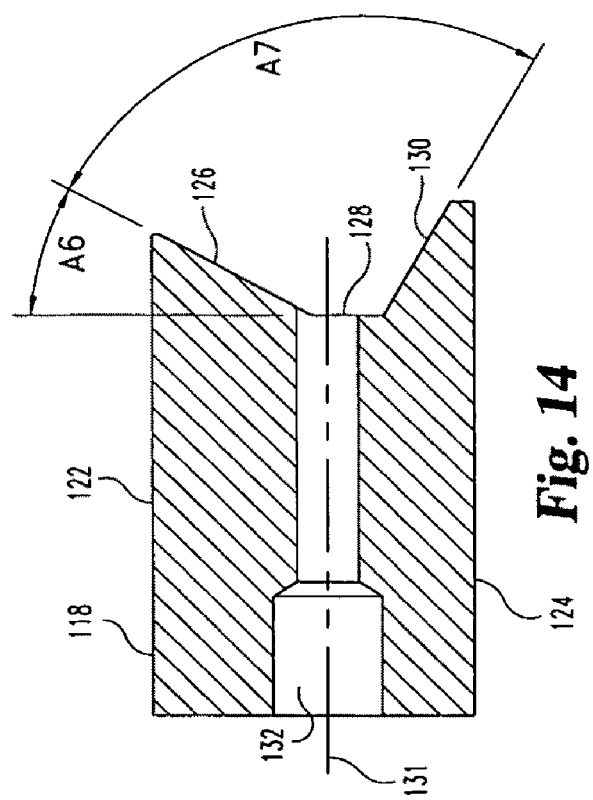
FIG. 14 is a cross-sectional view taken along line 14-14 of FIG. 12.
Figure 12:
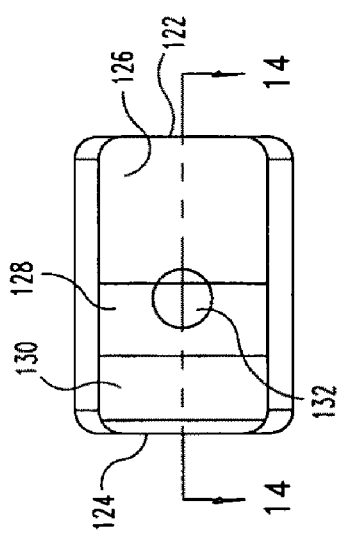
FIG. 12 is an end view of the distal guide of FIG. 10.
Figure 13:
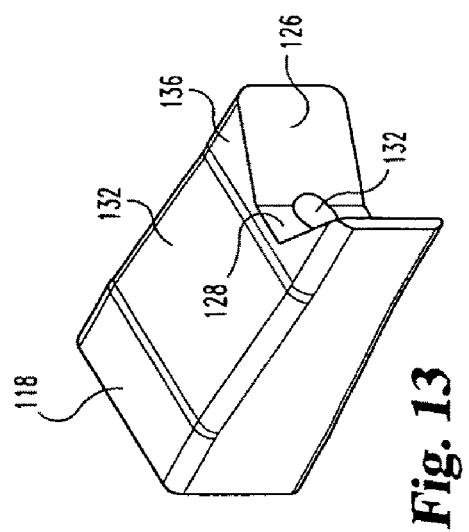
FIG. 13 is a perspective view of the distal guide of FIG. 12.
Figure 17:
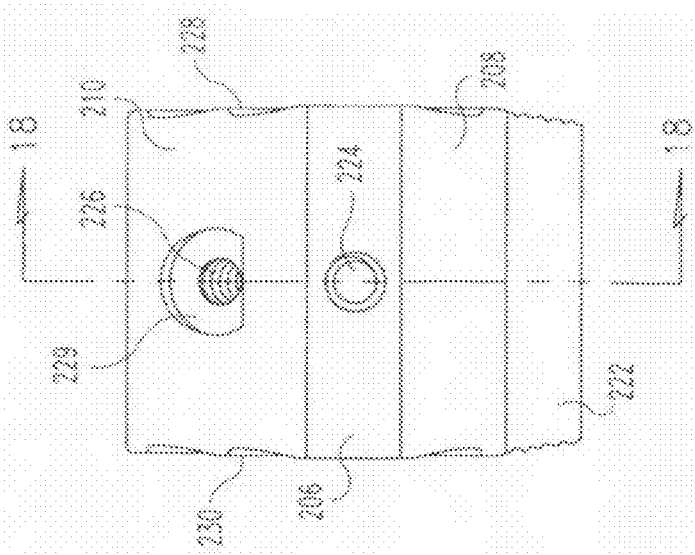
FIG. 17 is an end view of the implant of FIG. 16.

Referring now to FIGS. 12-14, distal guide 118 includes a central driving surface 128 substantially perpendicular to longitudinal axis 131 and the planes of side walls 122 and 124. Distal guide 118 further includes a first oblique driving surface 126 disposed at an angle A6 with respect to surface 128. In a preferred aspect, angle A6 is approximately 30 degrees. Distal guide 118 further includes a second angled driving surface 130 disposed at an angle A7 with respect to driving surface 126. In a preferred embodiment, angle A7 is approximately 90 degrees.

Referring now to FIGS. 15(a) and 15(b), implant inserter 110 is shown here connected with implant 10. Implant 10 is coupled to implant inserter 110 by engagement of externally threaded portion 120 of the inner shaft with internally threaded opening 44. Driving surfaces 126, 128, and 130 of distal guide 118 substantially engage surfaces 26, 22, and 18, respectively, of implant 10. It will be understood that driving surfaces of distal guide 118 are configured to substantially mate with the external surfaces of implant 10 such that force transmitted on the implant inserter tending to urge the implant into the disc space is substantially transmitted to implant 10. Additionally, angled side walls 126 and 130 inhibit rotation of implant 10. Further, in a preferred aspect, substantially parallel side walls 20 and 28 of implant 10 are in substantial parallel alignment and co-planar with opposing parallel side walls 122 and 124 of distal guide 118. Width W2 of distal portion 118 is substantially equal to or greater than the width D6 between opposing side walls 20 and 28 of implant 10.

Referring now to FIGS. 16-19(b), a further embodiment of an implant according to the present invention is shown. Implant 200 includes an upper bearing surface 228 and opposing lower bearing surface 230. Each of the upper and lower bearing surfaces include anti-migration members. In a preferred aspect of the invention, the anti-migration members are comprised of buttressed ridges extending substantially perpendicular to side walls 212 and 220. Still more preferably, upper and lower bearing surfaces 228 and 230 extend at an angle A25 with respect to one another forming a tapered implant. It is contemplated that angle A25 may have a variety of angles, but in a preferred embodiment specifically adapted for establishing and maintaining lumbar lordosis, angle A25 is approximately 8 degrees. Further, the implant has a maximum height of H20, which in a preferred aspect is approximately 21 mm.

As with the implant according to the first embodiment shown in FIG. 1, implant 200 includes two pair of opposing parallel side walls. Specifically, side wall 212 opposes substantially parallel side wall 220. Similarly, angled side walls 214 and opposing angled side wall 222 are in substantially parallel alignment. Side wall 222 extends at an angle A23 with respect to side wall 220. Angled side wall 214 extends at an angle A21 with respect to side wall 212. In a preferred aspect, angles A21 and A23 are substantially identical. Still more preferably, angles A21 and A23 are approximately 30 degrees. Implant 200 further includes end wall 216 and unmachined portion 215 extending between end wall 216 and angled wall 214. A further unmachined portion maintaining substantially the natural shape of donor bone 202 includes wall portion 218 extending between end wall 216 and side wall 220.

Figure 16:
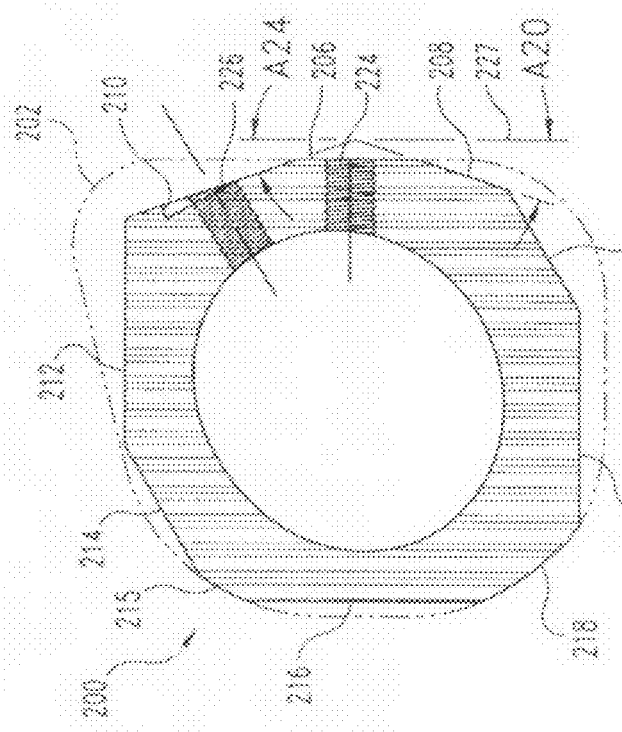
FIG. 16 is a top view of a further embodiment of an implant according to the present invention.
Figure 19A:
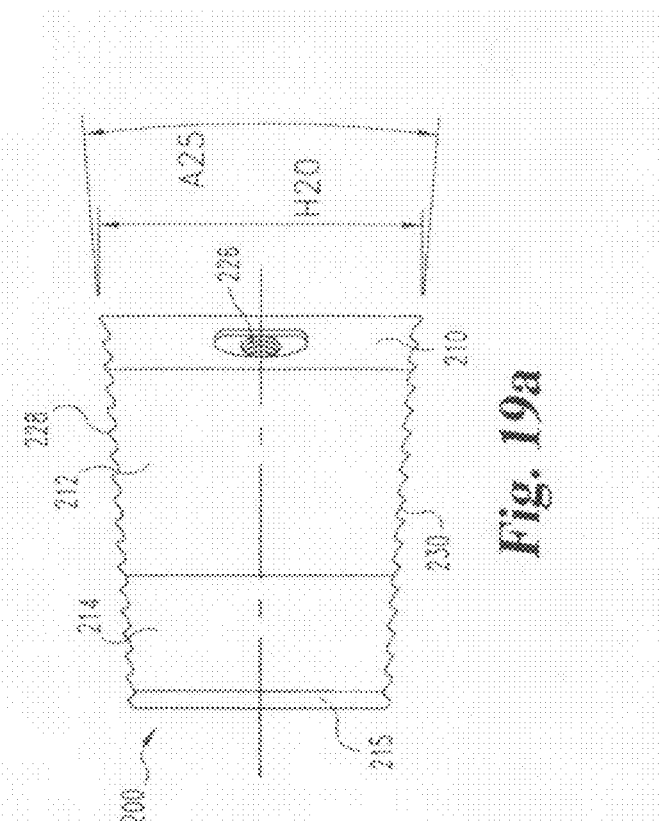
FIG. 19(a) is a side view of the implant of FIG. 16.
Figure 18:
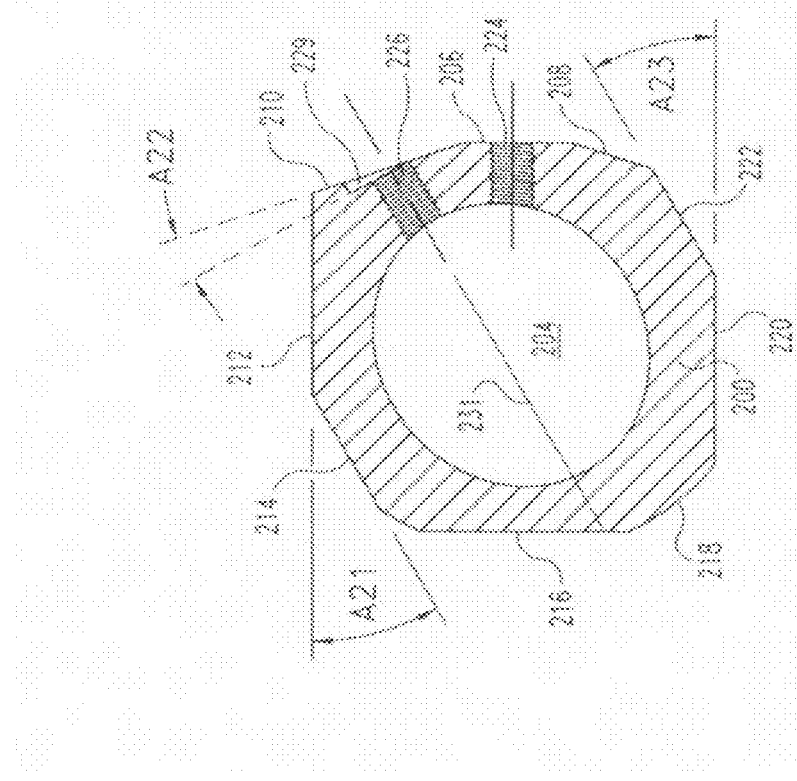
FIG. 18 is a cross-sectional view taken along line 18-18 of FIG. 17.
Figure 20A:
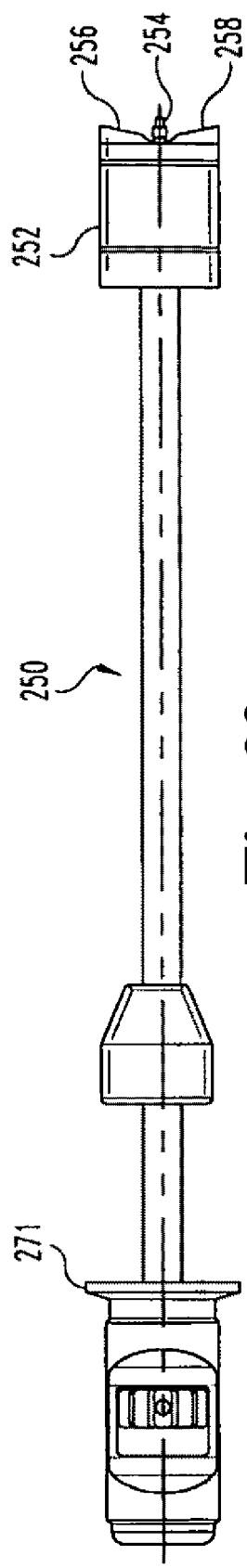
FIG. 20(a) is a top view of a further embodiment of an implant inserter according to the present invention.
Figure 20B:
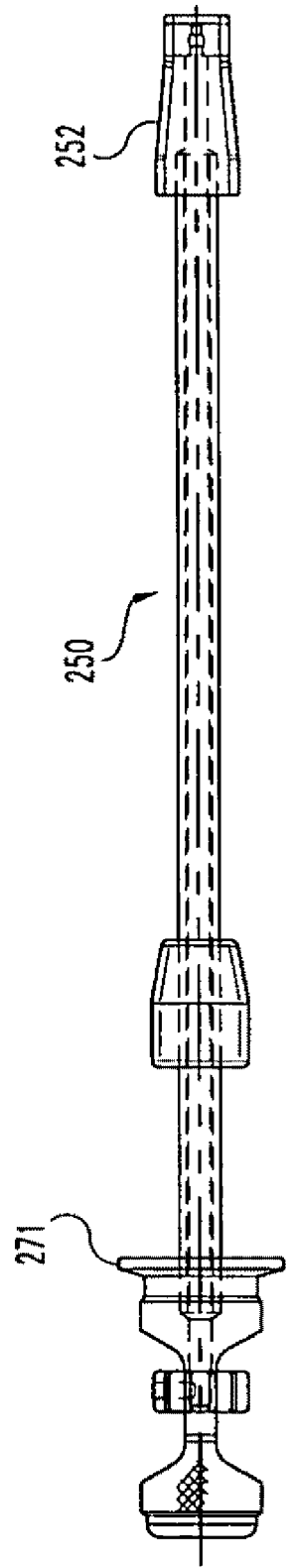
FIG. 20(b) is a side view of the implant inserter of FIG. 20(a).
Figure 25A:
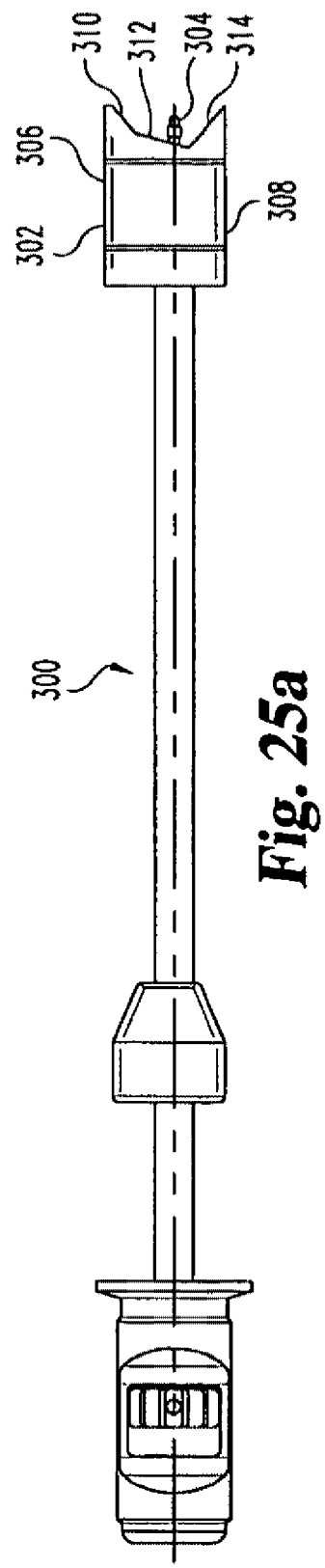
FIG. 25(a) is a top view of an alternative embodiment of an implant inserter according to the present invention.
Figure 25B:
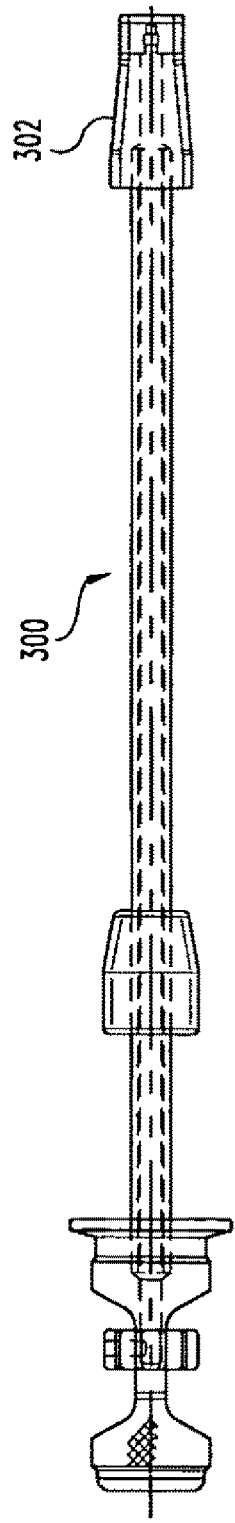
FIG. 25(b) is a side view of the implant inserter of FIG. 25(a).
Figure 26:
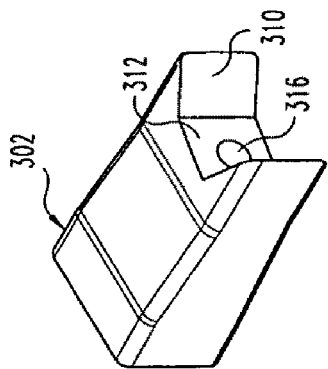
FIG. 26 is a perspective view of a distal guide of the implant inserter of FIG. 25(a).
Figure 28:
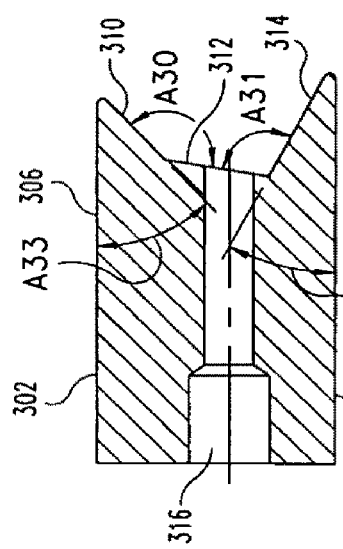
FIG. 28 is a cross-sectional view of the distal guide taken along line 28-28 of FIG. 27(b).
Figure 27A:
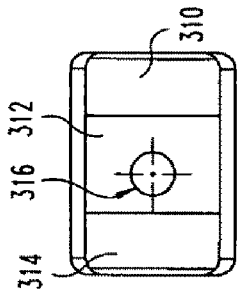
FIG. 27(a) is an end view of the distal guide of FIG. 26.
Figure 27B:
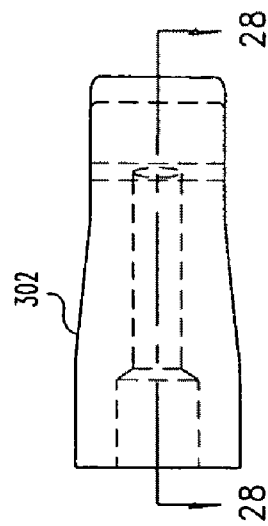
FIG. 27(b) is a side view of the distal guide of FIG. 26.
Figure 27C:
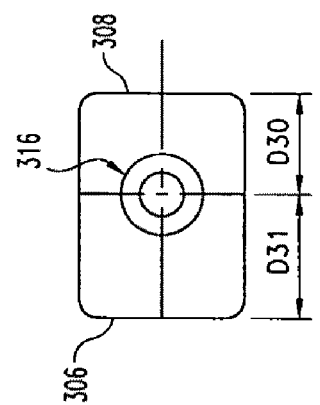
FIG. 27(c) is a rear end view of the distal guide of FIG. 26.

The driving walls of implant 200 have been modified in comparison to the implant of FIG. 1. Specifically, implant 200 includes a short drive wall 206 extending generally perpendicular to longitudinal axis 223. An internally threaded opening 224 is formed extending substantially along and in alignment with longitudinal axis 223. It is contemplated that driving wall 206 may be substantially unmachined and may include arcuate portions such as those found in the naturally occurring outer portion of donor bone 202. Referring to FIG. 16, angled driving walls 210 and 208 extend away from reference line 227 at an angle of A20 and A24, respectively. In a preferred embodiment, angles A20 and A24 are substantially identical. Still more preferably, angles A20 and A24 are substantially 18 degrees. Angled driving wall 210 further includes a recess surface 229 extending into surface 210 at an angle of A22. Preferably, angle A22 is approximately 12 degrees, thereby making surface 229 substantially perpendicular to angled side walls 214 and 222. Referring more specifically to FIG. 18, an internally threaded bore 226 is defined through the implant extending along axis 231. Axis 231 extends in substantial parallel alignment with side walls 214 and 222. In a preferred aspect, implant 200 is asymmetrical about axis 231. More specifically, in a preferred aspect of the invention axis 231 is approximately 12 mm from angled side wall 214 and approximately 14.5 mm from angled side wall 222. Implant 200 further includes central opening 204, which as previously described, will typically be defined by the naturally occurring medullary canal formed in the donor bone graft.

Referring now to FIGS. 20(a)-21(c), a straight implant inserter according to another aspect of the present invention is illustrated. Implant inserter 250 is substantially identical to the implant inserter of FIG. 5 with the exception of distal guide 252. Distal guide 252 includes a first angled drive surface 256 and an opposing angled drive surface 258 separated from the first drive surface by a concave surface 260. Surfaces 256 and 258 each extend at an angel A26 with respect to reference line 261 (FIG. 21(c)). Reference line 261 is substantially perpendicular to the surface of side walls 257 and 259. In a preferred aspect, angle A26 is substantially 18 degrees to matingly engage corresponding surfaces on implant 200. Distal guide 252 further includes an internal bore 262 extending through surface 260 adapted to receive the inner shaft. The inner shaft has an externally threaded portion 254 extending beyond distal guide 252.

Referring now to drawing FIGS. 22(a) and 22(b), implant inserter 250 is shown selectively coupled to implant 200. Distal guide 252 abuttingly engages implant 200. More specifically, angled drive surfaces 256 and 258 abuttingly engage angled drive surfaces 210 and 208, respectively. It will be understood that angled surfaces act to inhibit rotation of implant 200. Angled surfaces 256 and 258 limit rotation of the implant about the longitudinal axis of the inserter as the threaded post is engaged to implant 200 and rotation of the implant about itself as force is applied to urge the implant into the disc space. Thus, the angled drive surfaces provide secure engagement with the implant without the need for additional openings that may weaken the implant walls. Concave surface 260 is intended to be spaced from naturally occurring surface 206 such that machining of surface 206 is not required to provide the requisite clearance. Further, by spacing the driving walls from the wall having the threaded opening, force applied to the implant during insertion is concentrated away from the implant opening thereby having less tendency to cause fracture. This may be particularly beneficial where somewhat brittle materials, such as bone or ceramics, are used to form the implant. As shown in FIGS. 22(a)-(b), with implant 200 securely engaged with driver 250, opposing implant side walls 200 and 220 are in substantial alignment with implant driver side walls 257 and 259. It will be understood that by providing angled driving surfaces rather than a single planar drive surface, more of the natural architecture of the bone may be maintained, thereby increasing the strength of the implant. While angled drive surfaces are shown as substantially planar surfaces it will be understood that they may also be arcuate, concave, convex, or complex surfaces.

Implant 200 may be inserted into a vertebral disc space properly prepared for receipt from a direct anterior approach. As shown in FIG. 23(b), a distraction window 268 is disposed adjacent a vertebral body V1 with distraction extensions 270 and 272 extending into the vertebral disc space (the opposing upper vertebra is not shown). Guide tube 262 is selectively coupled to distraction window 268. Distraction window and guide tube define a substantially rectangular working channel (not shown) substantially confirming to the dimensions of the distal guide 252. Inserter 250 with selectively coupled implant 200 attached thereto may then be inserted through guide tube 266 and distraction window 268 and guided to the disc space. Implant inserter is slidably advanced in the guide tube 266 with distal guide maintaining alignment until stop 271 engages the distal end 273 of guide tube 266. Implant 200 will thereby be positioned in the proper location in the disc space with the intended orientation. The thumb wheel of implant inserter 250 may then be rotated to threadedly disengage the inserter from implant 200. Once implant inserter 250 has been disengaged from implant 200. The inserter may be removed from the guide tube and distraction window. Guide tube 266 and distraction window 268 may then be removed from the disc space.

Referring now to FIGS. 24(a)-24(c), implant 200 is shown disposed in a prepared end plate of vertebral V1. It will be understood that an opposed vertebra is disposed above the implant creating a disc space, but the upper opposed vertebra has been removed from the illustration for the purpose of clarity. Implant 200 is shown disposed in channel C1 defined in the end plate of vertebra V1. One method of forming channel C1 is disclosed in Provisional Application entitled "Instruments and Techniques for Disc Space Preparation," filed on Feb. 22, 2000, which is incorporated herein by reference. Channel C1 extends in a direction extending from the anterior to the posterior portion of the vertebra and is configured for direct anterior insertion of an implant. End surface 216 is shown in substantial alignment with posterior portion 274 of channel C1. Thus, end surface 216 is disposed substantially adjacent the posterior portion 275 of vertebra V1. Side walls 212 and 220 are disposed laterally with respect to vertebra V1. Thus, implant 200 is disposed in the disc space between vertebra V1 and the upper opposed vertebra (not shown) such that the taper between opposed bone engaging surfaces 228 and 230 is in proper alignment and orientation to maintain the appropriate angular relationship between the opposing vertebral bodies.

Referring now to FIGS. 25(a)-28, there is shown an implant inserter 300 adapted for insertion of implant 200 from an anterior-oblique approach to the spine. Inserter 300 includes features also found in implant inserter 250 with the exception that distal guide 302 has been configured to permit engagement with an implant for oblique insertion. Distal guide 302 includes a first angled drive surface 310 disposed at an angle A33 with respect to side wall 306. In a preferred embodiment, A33 is approximately 42 degrees. A second angled drive surface 314 is disposed at an angle A32 with respect to side wall 308. In the preferred aspect, A32 is approximately 30 degrees. A third angled surface 312 is disposed at an angle A30 with respect to angled drive surface 310 and an angle A31 with respect to angled drive surface 314. In a preferred embodiment, angle A30 is approximately 144 degrees and angle A31 is approximately 108 degrees. Additionally, an internal bore 316 is formed through distal guide 302. Bore 316 is formed a distance D30 from side wall 308 and a distance D31 from side wall 306. In a preferred aspect of the invention, D31 is greater than the distance D30 such that bore 316 is offset with respect to the longitudinal axis of guide 302. More specifically, distance D30 is approximately 12 mm and distance D31 is approximately 15 mm.

Referring to FIGS. 29(a) and 29(b), implant inserter 300 is shown selectively coupled to implant 200. Angled driving surfaces 310 and 314 are in abutting engagement with driving surfaces 212 and 208. It will be noted that angled surface 312 and 310 have sufficient length such that side wall 206 is not intended to be in substantial contact with the implant driver. Further, it is contemplated that surface 312 may be spaced slightly from wall 210 to limit stress on the implant adjacent opening 226. Implant 200 is aligned with distal guide 302 such that opposing side walls 214 and 222 are in substantial alignment with side walls 308 and 306, respectively, of distal guide 302. Moreover, angled driving surfaces 310 and 314 cooperate to limit implant rotation.

Referring now to FIGS. 30(a)-31(c), a distraction window 342 is disposed in a disc space created by vertebra V2 and an opposing upper vertebra (not shown) with distraction extensions 344 and 346 extending into the disc space. Distraction window 342 is positioned in the disc space from an anterior-oblique angle approach to the spine. Specifically, reference line 348 represents a direct anterior approach to the spine, in substantial alignment with the sagittal plane. In the anterior-oblique approach, distraction window 342 is positioned into the disc space from an angled approach shown by angle A35. In a preferred embodiment, with opposing angled side walls disposed at an approximately 30 degree angle, angle A35 is approximately 30 degrees. A guide tube 340 is selectively coupled to distraction window 342, thereby forming a substantially rectangular working channel into the disc space. Inserter 300 with interconnected implant 200 is then inserted through guide sleeve 340 until implant 200 is disposed in the disc space in preformed channel C2. The guide sleeve has dimensions substantially corresponding to the implant dimensions, thereby limiting the amount of tissue, vessels and other structures that must be removed or retracted for placement of the implant. The inner shaft is then rotated to release implant inserter from implant 200. The implant inserter, guide tube, and distraction window may then be removed. The orientation of implant 200 in comparison to vertebra V2 is substantially identical to the orientation of implant 200 with respect to vertebra V1 shown in FIGS. 24(a)-24(c). End wall 216 is in substantial alignment with posterior portion 274 of channel C2. End wall 216 is disposed substantially adjacent posterior portion 275 of vertebra V2. Further, opposed side walls 212 and 250 are in substantial lateral alignment with the lateral portions of vertebra V2. Thus, it will be understood that implant 200 is positioned in the disc space with the tapering surfaces 228 and 230 extending in the proper orientation to provide maintenance of angulation between vertebra V2 and the opposing upper vertebra (not shown).

While not shown by illustration, it will be understood that the implants described herein may be inserted from a direct lateral approach to the spine. The same orientation in the disc space may be achieved regardless of the direction of insertion and the guiding instruments used.

Thus, the present invention provides an implant having multiple facets or substantially parallel side walls allowing uniform orientation of the implant in the disc space although it is inserted by multiple, often guided, approaches to the spine. Specifically, the embodiments of the implants according to the present invention permit insertion from a direct anterior, oblique-anterior and a direct lateral approach to the spine. While preferred embodiments of the invention has disclosed three pair of substantially parallel side walls disposed at a various angles, it is contemplated that more than three pair of substantially parallel side walls could be utilized to provide for implant insertion from a plurality of angles. Further, while a particular angle of 30 degrees has been utilized for the purposes of illustration in a preferred embodiment, it will be understood that any oblique angle might be utilized to provide for insertion from multiple approaches from the spine.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal implant for implanting into a disc space of a spine, comprising:
    an implant body having first, second and third pairs of substantially parallel sidewalls constructed and arranged to permit insertion of said implant body into the disc space at least from a direct anterior approach to the spine and an oblique angle to the spine, wherein said implant body includes a leading end and an opposite trailing end for engagement by an inserter, and said leading end includes a first unmachined arcuate portion connecting a first sidewall of said second pair of substantially parallel sidewalls to a first sidewall of said first pair of substantially parallel sidewalls and a second unmachined arcuate portion connecting said first sidewall of said second pair of substantially parallel sidewalls to a first sidewall of said third pair of substantially parallel sidewalls, said first pair of substantially parallel sidewalls extending parallel to a longitudinal axis of said implant body, wherein said first and second sidewalls of said first pair of substantially parallel sidewalls are longitudinally offset from one another along said longitudinal axis; and
    wherein said implant body is tapered.

2. The implant of claim 1, wherein said implant body has an upper anti-migration surface and a lower anti-migration surface adapted to minimize implant migration.

3. The implant of claim 1, wherein:
    said implant body is formed of bone.

4. The implant of claim 1, wherein said implant body has a threaded bore defined therein and a second bore defined therein parallelly spaced apart from said threaded bore, said second bore being adapted to receive a pin to minimize implant rotation.

5. The implant of claim 1, wherein said implant body has a central opening defined therein.

6. The implant of claim 1, wherein said implant body includes:
    said second pair of substantially parallel sidewalls disposed transversely with respect to said first pair of sidewalls;
    an angled sidewall extending between a second sidewall of said first pair of substantially parallel sidewalls and a second sidewall of said second pair of substantially parallel sidewalls;
    said leading end being opposite said angled sidewall; and
    said third pair of substantially parallel sidewalls including said first sidewall of said third pair of substantially parallel sidewalls extending from said second sidewall of said first pair of substantially parallel sidewalls toward said leading end and a second one of said third pair of substantially parallel sidewalls extending from said second sidewall of said second pair of substantially parallel sidewalls to said first sidewall of said first pair of substantially parallel sidewalls.

7. The implant of claim 6, wherein said implant body has a threaded bore defined therein and a second bore defined therein that is spaced apart from and parallel to said threaded bore, wherein said threaded bore and said second bore are both formed in said implant body parallel with said first pair of substantially parallel sidewalls and further comprising a second threaded bore formed in said implant body parallel with said third pair of substantially parallel sidewalls.

8. The implant of claim 6, wherein said implant body defines a first insertion tool bore and a second insertion tool bore, said first tool bore extending substantially parallel to said first pair of sidewalls and said second tool bore extending substantially parallel to said third pair of substantially parallel sidewalls.

9. The implant of claim 8, wherein said implant body defines a third bore that is spaced apart from and parallel to said first insertion tool bore.

10. The implant of claim 6, wherein said second pair of substantially parallel sidewalls extends substantially perpendicular to said first pair of substantially parallel sidewalls and said angled sidewall is oblique to each of said first pair and said second pair of substantially parallel sidewalls.

11. The implant of claim 10, wherein said angled sidewall extends obliquely to said longitudinal axis of said implant body.

12. A spinal implant for implanting into a disc space of a spine, comprising:
    an implant body extending along a longitudinal axis between a leading end and an opposite trailing end, said implant body including:
        a first pair of substantially parallel sidewalls extending parallel to said longitudinal axis of said implant body;
        a second pair of substantially parallel sidewalls disposed transversely with respect to said first pair of sidewalls;
        an angled sidewall extending obliquely to said longitudinal axis between a first sidewall of said first pair of substantially parallel sidewalls and a first sidewall of said second pair of substantially parallel sidewalls, wherein said leading end is opposite of said angled sidewall and said first sidewall of said second pair of substantially parallel sidewalls; and
        a third pair of substantially parallel sidewalls, a first sidewall of said third pair of substantially parallel sidewalls extending from said first sidewall of said first pair of substantially parallel sidewalls toward said leading end and a second sidewall of said third pair of substantially parallel sidewalls extending toward said leading end from said first sidewall of said second pair of substantially parallel sidewalls to a second sidewall of said first pair of substantially parallel sidewalls, wherein said first and second sidewalls of said first pair of substantially parallel sidewalls are longitudinally offset from one another along said longitudinal axis; and wherein said implant body is formed of bone and includes a first unmachined arcuate portion connecting a second sidewall of said second pair of substantially parallel sidewalls to said second sidewall of said first pair of substantially parallel sidewalls and a second unmachined arcuate portion connecting said second sidewall of said second pair of substantially parallel sidewalls to said first sidewall of said third pair of substantially parallel sidewalls.

13. The implant of claim 12, wherein said implant body has an upper anti-migration surface and a lower anti-migration surface adapted to engage adjacent vertebral endplates and minimize implant migration in a spinal disc space.

14. The implant of claim 12, wherein said implant body has a threaded bore defined therein and a second bore defined therein that is parallel and spaced apart from said threaded bore.

15. The implant of claim 14, wherein said threaded bore and said second bore are both formed in said implant body parallel with said first pair of substantially parallel sidewalls and further comprising a second threaded bore formed in said implant body parallel with said third pair of substantially parallel sidewalls.

16. The implant of claim 12, wherein said implant body has a central opening defined therein opening at opposite upper and lower surfaces of said implant body.

17. The implant of claim 12, wherein said implant body defines a first insertion tool bore and a second insertion tool bore, said first tool bore extending substantially parallel to said first pair of sidewalls and said second tool bore extending substantially parallel to said third pair of substantially parallel sidewalls.

18. The implant of claim 12, wherein said second pair of substantially parallel sidewalls extends substantially perpendicular to said first pair of substantially parallel sidewalls and said angled sidewall is oblique to each of said first pair and said second pair of substantially parallel sidewalls.

19. The implant of claim 18, wherein said angled sidewall extends obliquely to said longitudinal axis of said implant body.

* * * * *